United States Patent
Nair et al.

(10) Patent No.: US 11,642,319 B2
(45) Date of Patent: May 9, 2023

(54) TARGETED NANOGELS FOR URINARY BLADDER THERAPIES

(71) Applicant: THE REGENTS OF THE UNIVERSITY OF COLORADO, Denver, CO (US)

(72) Inventors: Devatha P. Nair, Denver, CO (US); Dmitri Simberg, Centennial, CO (US); Manju Saraswathy, Aurora, CO (US)

(73) Assignee: THE REGENTS OF THE UNIVERSITY OF COLORADO, Denver, CO (US)

(*) Notice: Subject to any disclaimer, the term of this patent is extended or adjusted under 35 U.S.C. 154(b) by 711 days.

(21) Appl. No.: 16/496,727

(22) PCT Filed: Mar. 23, 2018

(86) PCT No.: PCT/US2018/024049
§ 371 (c)(1),
(2) Date: Sep. 23, 2019

(87) PCT Pub. No.: WO2018/175899
PCT Pub. Date: Sep. 27, 2018

(65) Prior Publication Data
US 2020/0030244 A1    Jan. 30, 2020

Related U.S. Application Data

(60) Provisional application No. 62/476,270, filed on Mar. 24, 2017.

(51) Int. Cl.
| | | |
|---|---|---|
| *A61K 47/69* | (2017.01) | |
| *A61K 9/51* | (2006.01) | |
| *A61K 9/00* | (2006.01) | |
| *A61K 9/06* | (2006.01) | |
| *A61K 31/496* | (2006.01) | |
| *A61K 31/7036* | (2006.01) | |
| *A61K 41/00* | (2020.01) | |
| *C08J 3/075* | (2006.01) | |

(52) U.S. Cl.
CPC ......... *A61K 9/5138* (2013.01); *A61K 9/0034* (2013.01); *A61K 9/06* (2013.01); *A61K 9/5192* (2013.01); *A61K 31/496* (2013.01); *A61K 31/7036* (2013.01); *A61K 41/0042* (2013.01); *A61K 47/6903* (2017.08); *C08J 3/075* (2013.01); *C08J 2300/00* (2013.01); *C08J 2325/14* (2013.01)

(58) Field of Classification Search
CPC ...... A61K 9/5138; A61K 9/0034; A61K 9/06; A61K 9/5192; A61K 9/5146; A61K 31/496; A61K 31/7036; A61K 38/13; A61K 41/0042; A61K 47/6903; A61K 47/34; A61K 47/62; A61L 2300/25; A61L 26/0014; A61L 26/0066; A61L 26/008; C08J 3/075; C08J 2300/00; C08J 2325/14
See application file for complete search history.

(56) References Cited

U.S. PATENT DOCUMENTS

| | | | |
|---|---|---|---|
| 7,671,156 B2 | 3/2010 | Phelan et al. | |
| 9,138,383 B1* | 9/2015 | Stansbury | ............... A61K 6/887 |
| 2012/0208742 A1* | 8/2012 | Primiano | ............... C12N 15/87 |
| | | | 977/773 |
| 2015/0051310 A1 | 2/2015 | Stansbury | |
| 2018/0250438 A1* | 9/2018 | Jabbari | ................... A61L 27/58 |

FOREIGN PATENT DOCUMENTS

| | | |
|---|---|---|
| KR | 20140103426 A | 8/2014 |
| WO | 2016033295 A1 | 3/2016 |

OTHER PUBLICATIONS

Ryu et al.; Biomacromolecules, 2012, vol. 13, p. 1515-1522.*
Chan; Investigation of Novel Thiol "Click" Reactions, 2009, p. i-232.*
Al-Motawa et al.; Frontiers in Pharmacology, 2020, vol. 11, p. 1-12.*
International Search Report dated Jul. 30, 2018; International Application No. PCT/US2018/24049; International Filing Date Mar. 23, 2018 (5 pgs).
Written Opinion dated Jul. 30, 2018; International Application No. PCT/US2018/24049; International Filing Date Mar. 23, 2018 (8 pgs).

* cited by examiner

*Primary Examiner* — Robert S Jones, Jr.
(74) *Attorney, Agent, or Firm* — Cantor Colburn LLP

(57) ABSTRACT

Methods for intravesical administration of a therapeutic agent including application of a photoactive nanogel to the mucosal surfaces of the bladder and/or intravesical application of cell-penetrating peptides. Photoactive nanogels may be aggregated by exposure to ultraviolet light, either in vitro or in vivo, to provide controlled or extended release of a therapeutic agent, such as an antibiotic.

2 Claims, 16 Drawing Sheets

Specification includes a Sequence Listing.

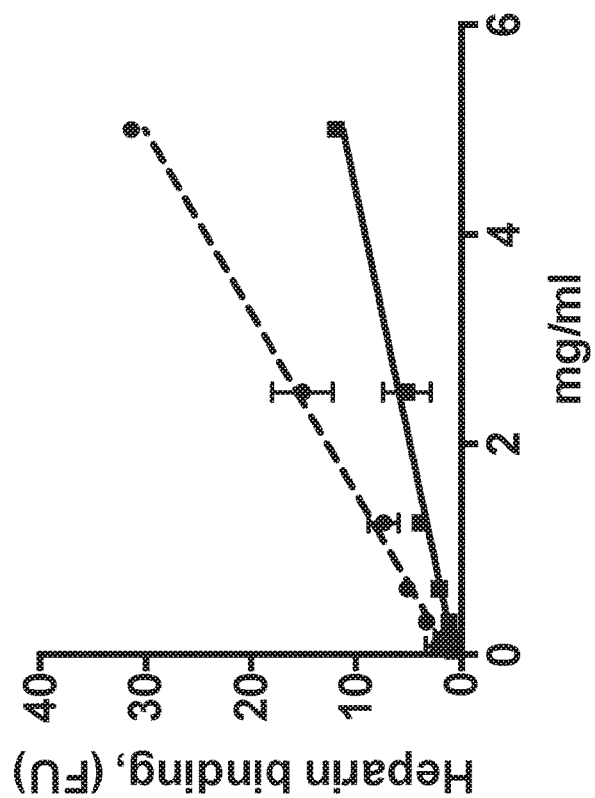
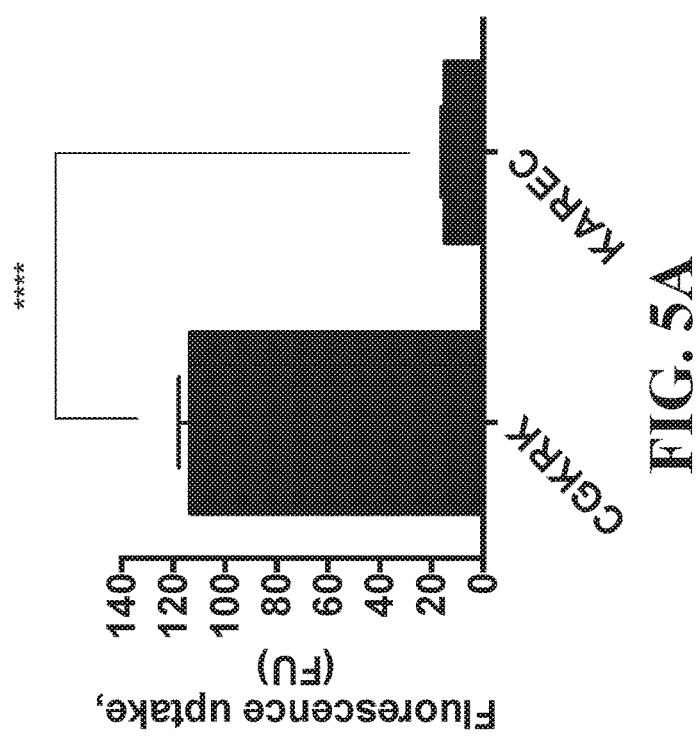
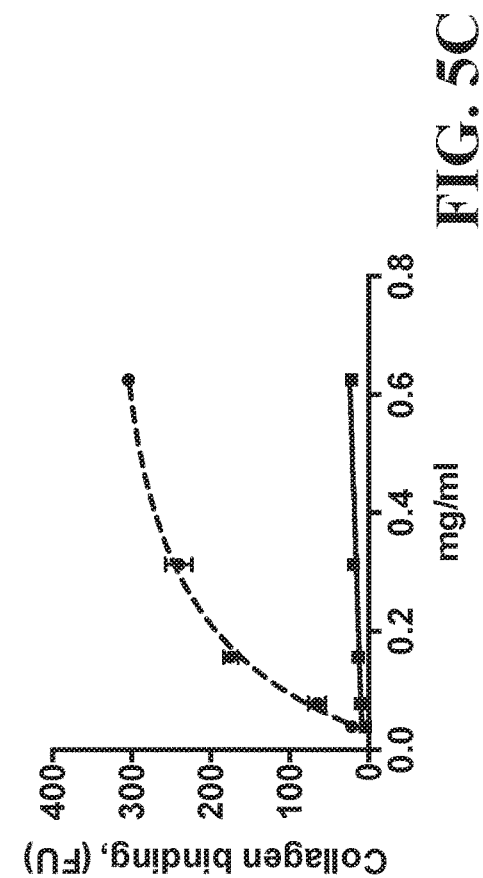
FIG. 5A
FIG. 5B
FIG. 5C

SEQUENCE LISTING

```
<160> NUMBER OF SEQ ID NOS: 2

<210> SEQ ID NO 1
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 1

Cys Gly Lys Arg Lys
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 2

Lys Ala Arg Glu Cys
1               5
```

TARGETED NANOGELS FOR URINARY BLADDER THERAPIES

CROSS-REFERENCE TO RELATED APPLICATIONS

This application is a U.S. National Phase application of PCT/EP2018/024049 filed on Mar. 23, 2018, claiming the benefit of U.S. Ser. No. 62/476,270, filed on Mar. 24, 2017, both of which are incorporated herein by reference in their entireties.

FIELD OF THE INVENTION

This disclosure relates to methods for improved delivery and penetration of a drug on a mucosal surface, and in particular, methods for improving intravesical (within the bladder) drug delivery and penetration by use of photoactive nanogels and/or cell-penetrating peptides.

BACKGROUND

For many diseases and pathological conditions of the bladder, intravesical (within the bladder) administration is the preferred method for delivering therapeutic agents. In the intact human bladder, umbrella cells in the upper mucosal layer form a tight barrier that prevents the systemic absorption of molecules and solutes; although this barrier greatly improves the safety of intravesical therapies, it also limits the penetration of the therapeutic agent into the bladder urothelium.

A number of approaches have been explored for enhancing delivery of drugs to the urothelium. For instance, some solutions have utilized dimethyl sulfoxide (DMSO) to enhance the accumulation of micelles of an active agent, such as paclitaxel, in the mucosal layer, or have disrupted the barrier function of the urothelium and enhanced penetration of molecules and nanoparticles into the urothelium by means of protamine sulfate, ethanol, dilute acid, or distention of the bladder with fluid. These approaches can pose significant risks to the patient and often do not result in homogeneous penetration of the active agent into the urothelium, necessitating the development of improved intravesical drug delivery approaches.

Of particular interest is the intravesical administration of drugs to treat urinary tract infections, especially infections caused by uropathogenic *Escherichia coli* (UPEC). UPEC infections are difficult to clear with traditional antibiotics because the bacteria interact with superficial bladder cells to form dormant intracellular colonies, making the infection relatively insusceptible to antibiotics and immune response. Thus, the dose of antibiotic needed to effectively clear UPEC infections can be very high and does not necessarily affect the dormant intracellular colonies, making recurrent infection common. As a result, a delivery mechanism that allows the antibiotic to penetrate the cell membrane of the infected superficial bladder cells is highly desirable.

Photoactive nanogels have lately shown promise as a means of enhancing the mucosal adhesion of a drug solution and providing a controlled drug release profile. In particular, photoactive nanogels can inter-react in situ due to exposure to an ultraviolet (UV) light source; in the intravesical context, a photoactive nanogel drug solution may be administered intravesically and then exposed to UV light through a catheter. After the reaction, the nanogels can be fixed in place on a mucosal membrane, such as that of the urinary bladder, and allow sustained release of the drug over a longer period. Because nanogels can encapsulate and carry significant quantities of bioactive molecules, such as drugs, nucleic acids, and proteins, to a desired site, nanogels have immense potential for use in drug delivery.

Additionally, recent research has disclosed the effectiveness of cell-penetrating peptides in improving delivery of therapeutic proteins and nucleic acids to the bladder. However, although it is well-known that cell-penetrating peptides aid in delivery of drugs when the mucosae are intact, the ability of cell-penetrating peptides to penetrate the mucosal layers 1) following damage to the urothelium and 2) to enable the controlled and targeted delivery of a therapeutic within the layers of the urothelium has not been studied in great detail to date. The effectiveness of cell-penetrating peptides when the urothelium is damaged is an important consideration because a number of significant bladder diseases and pathological conditions result in damage to or destruction of the urothelium; for instance, interstitial cystitis is manifested by leaky and dysfunctional mucosa, and trans-urethral resection (TUR) of non-invasive bladder carcinoma in situ (CIS) entails scratching the urothelium off together with the cancerous lesion to expose the lamina propria.

Thus, there is a need in the art for improving retention of an intravesically-administered drug in the bladder, and controlling release of the drug, by combining the drug with a photoactive nanogel. There is a further need in the art for a cell-penetrating peptide-based administration technique that is effective to deliver a therapeutic agent when the mucosae are damaged, destroyed, or dysfunctional.

SUMMARY

It is one aspect of the present invention to provide a method for synthesizing a photoactive nanogel suitable for drug delivery, comprising mixing about 2 molar parts of 2-hydroxyethyl acetate, about 2 molar parts of styrene, and about 1 molar part of polyethyleneglycol dimethacrylate having a molecular weight of about 1,000 daltons (PEGDMA 1000) to form a starting mixture; dissolving the starting mixture in a mass of toluene equal to at least about two times a mass of the starting mixture to form a solution; adding azobisisobutyronitrile (AIBN) and 2-mercaptoethanol to the solution; exposing the solution to a first reaction temperature for a first reaction time to form a nanogel; and exposing the nanogel to a second reaction temperature for a second reaction time, in the presence of 2-isocyanatoethyl methacrylate (IEM) and dibutyltin diluarate (DBT), to form the photoactive nanogel.

In some embodiments, the mass of toluene may be equal to at least about four times the mass of the starting mixture.

In some embodiments, the first reaction temperature may be about 90° C.

In some embodiments, the first reaction time may be about 3 hours.

In some embodiments, the first reaction time may be about 4 hours.

In some embodiments, the second reaction temperature may be about 23° C.

In some embodiments, the second reaction time may be about 16 hours.

In some embodiments, the method may further comprise loading an active pharmaceutical ingredient onto the photoactive nanogel; and aggregating the loaded photoactive nanogel by exposing the loaded photoactive nanogel to ultraviolet light for at least about 10 minutes.

It is another aspect of the present invention to provide a photoactive nanogel suitable for drug delivery, made by a method comprising mixing about 2 molar parts of 2-hydroxyethyl acetate, about 2 molar parts of styrene, and about 1 molar part of polyethyleneglycol dimethacrylate having a molecular weight of about 1,000 daltons (PEGDMA 1000) to form a starting mixture; dissolving the starting mixture in a mass of toluene equal to at least about two times a mass of the starting mixture to form a solution; adding azobisisobutyronitrile (AIBN) and 2-mercaptoethanol to the solution; exposing the solution to a first reaction temperature for a first reaction time to form a nanogel; and exposing the nanogel to a second reaction temperature for a second reaction time, in the presence of 2-isocyanatoethyl methacrylate (IEM) and dibutyltin diluarate (DBT), to form the photoactive nanogel.

In some embodiments, the photoactive nanogel may have a molecular weight of at least about 10,000 daltons.

In some embodiments, the method may further comprise loading an active pharmaceutical ingredient onto the photoactive nanogel to create a loaded photoactive nanogel; and aggregating the loaded photoactive nanogel by exposing the loaded photoactive nanogel to ultraviolet light for at least about 10 minutes.

It is still another aspect of the present invention to provide a method for administration of an active pharmaceutical ingredient to a mammal, comprising mixing about 2 molar parts of 2-hydroxyethyl acetate, about 2 molar parts of styrene, and about 1 molar part of polyethyleneglycol dimethacrylate having a molecular weight of about 1,000 daltons (PEGDMA 1000) to form a starting mixture; dissolving the starting mixture in a mass of toluene equal to at least about two times a mass of the starting mixture to form a solution; adding azobisisobutyronitrile (AIBN) and 2-mercaptoethanol to the solution; exposing the solution to a first reaction temperature for a first reaction time to form a nanogel; exposing the nanogel to a second reaction temperature for a second reaction time, in the presence of 2-isocyanatoethyl methacrylate (IEM) and dibutyltin diluarate (DBT), to form a photoactive nanogel; loading an active pharmaceutical ingredient onto the photoactive nanogel; aggregating the loaded photoactive nanogel by exposing the loaded photoactive nanogel to ultraviolet light for at least about 10 minutes to form an aggregated pharmaceutical nanogel; and administering the aggregated pharmaceutical nanogel to the mammal. In related methods, the step of aggregating the loaded photoactive nanogel may be conducted in vivo by administering the loaded photoactive nanogel to the mammal and exposing the loaded photoactive nanogel to ultraviolet light to form an aggregated pharmaceutical nanogel in vivo. For example, the loaded photoactive nanogel may be administered intravesically followed by exposure to ultraviolet light provided into the bladder via a catheter to form the aggregated pharmaceutical nanogel in the bladder of the mammal.

The aggregated pharmaceutical nanogel may be administered to one or more mucosae of the mammal. The mammal may be a human.

It is yet another aspect of the present invention to provide a nanogel composition comprising at least one cell-penetrating peptide and at least one "payload," wherein the cell-penetrating peptide is conjugated to the nanogel, wherein the nanogel comprises a copolymer of 2-hydroxyethyl acrylate and urethane dimethacrylate.

In some embodiments, the at least one cell-penetrating peptide may comprise CGKRK (SEQ ID NO:1).

In some embodiments, the payload may comprise an active pharmaceutical ingredient.

It is a further aspect of the present invention to provide a method for intravesical administration of an active pharmaceutical ingredient to a patient, comprising providing a nanogel composition comprising at least one cell-penetrating peptide and at least one payload, wherein the cell-penetrating peptide is conjugated to the nanogel; and administering the composition to the patient such that the payload penetrates the bladder mucosae, wherein the patient has a focal injury of the bladder mucosae and suffers from at least one disease, disorder, or pathological condition of the bladder.

In some embodiments, the focal injury may comprise a wound.

In some embodiments, the at least one disease, disorder, or pathological condition may be selected from the group consisting of bladder cancer, interstitial cystitis, and urinary tract infection. In some embodiments, the at least one disease, disorder, or pathological condition may result in damage to or destruction of the urothelium such as interstitial cystitis manifested by leaky and dysfunctional mucosa, and trans-urethral resection (TUR) of non-invasive bladder carcinoma in situ (CIS).

In some embodiments, the payload may comprise at least one active pharmaceutical ingredient selected from the group consisting of antibiotics and chemotherapeutics. In some embodiments, the payload may comprise at least one active pharmaceutical ingredient selected from the group consisting of amitriptyline, amoxicillin, botulinum toxin, ceftriaxone, a cephalosporin, cimetidine, ciprofloxacin, clavulanic acid, cyclosporine A, dimethyl sulfoxide, a fluoroquinolone, fosfomycin, gentamicin, heparin, hydroxyzine, lidocaine, nitrofurantoin, pentosan polysulfate, sulfamethoxazole, triamcinolone, and trimethoprim.

The at least one cell-penetrating peptide may comprise the peptide CGKRK (SEQ ID NO:1).

The nanogel may comprise a copolymer of 2-hydroxyethyl acrylate and urethane dimethacrylate.

The nanogel may comprise a copolymer of hydroxyethyl acetate (HEA), polyethylene glycol dimethacrylate, and styrene.

One advantage of the present invention is that it provides nanogels that enable sustained, localized delivery of an antibiotic or other active pharmaceutical ingredient. By way of non-limiting example, antibiotics delivered intravesically according to the present disclosure may eradicate intracellular UPEC colonies and/or *Candida albicans* biofilms, leading to healing or healthy replacement of the urothelium and preventing recurrent urinary tract infection. In contrast to existing oral, intramuscular, and intravenous delivery systems for active pharmaceutical ingredients (e.g. antibiotics, anti-inflammatories, and chemotherapeutic drugs for the treatment of bladder cancer), which may have undesirably rapid release kinetics and/or fail to reach the targeted tissues, nanogel preparations according to the present invention can bind to and controllably release the active pharmaceutical ingredient for a period of at least about 48 hours, and in some embodiments at least about 120 hours.

The above-described benefits, embodiments, and characterizations are not necessarily complete or exhaustive, particularly as to the patentable subject matter disclosed herein. Other benefits, embodiments, or characterizations of the present disclosure are possible as set forth above, as described in the accompanying figures, and as in the description herein below. However, the Detailed Description of the Invention, the drawing figures, and the claims set forth herein, taken in conjunction with this Summary, exemplify aspects of the invention.

The accompanying drawings, which are incorporated in and constitute a part of the specification, illustrate embodiments of the disclosure and, together with the general description of the disclosure given above and the detailed description of the drawings given below, serve to explain the principles of the disclosure.

BRIEF DESCRIPTION OF THE DRAWINGS

FIGS. 5A through 5C illustrate the cell and stroma binding properties of the pentapeptide CGKRK (SEQ ID NO:1);

FIG. 9A shows that the release of FITC can be modulated via photoinduced crosslinking of the network as a function of dose (intensity×time) prior to delivery. FIG. 9B shows that the release of FITC from a nanogel can be controlled based on the exposure time (0, 30, 60, 90 secs) at 7 mW/cm-1 light at 365 nm.

DETAILED DESCRIPTION

Figure 1:
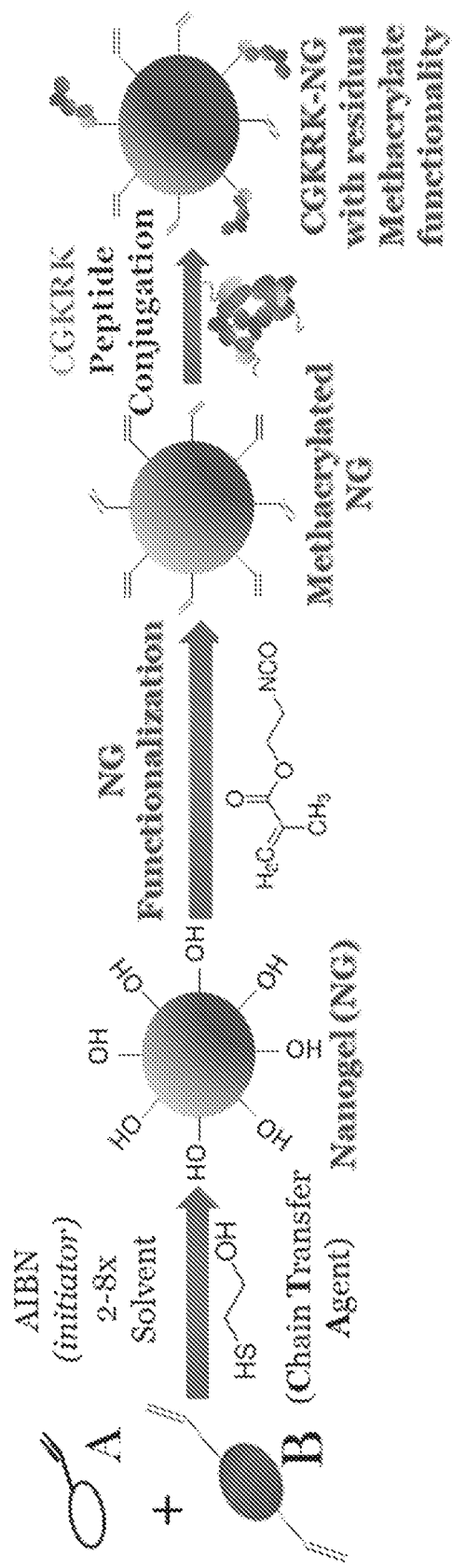
FIG. 1 is a schematic representation of a thermally initiated, solution polymerization synthesis route implemented typically reacts a monovinyl monomer (A, such as 2-hydroxyethyl acrylate) with a divinyl crosslinker (B, such as polyethyleneglycol dimethacrylate) in the presence of a chain transfer agent (CTA, such as 2-mercaptoethanol) to obtain cross-linked NG. The NG can be functionalized via an alcohol-isocyanate reaction between the residual OH groups (introduced via the choice of monomer or CTA) and 2-isocyanoethyl methacrylate. Subsequently, the photoreactive CGKRK (SEQ ID NO:1)-linked NG conjugates with residual methacrylate functionality can be generated via a thiol-methacrylate Michael-Addition reaction.

This disclosure provides a polymeric network having a particle size of less than 100 nanometers (a nanogel) that is safe for topical, local, and/or systemic delivery, and which can act as a carrier for drugs, such as antibiotics, and can also be targeted to intracellular delivery by conjugation of intracellular targeting molecules to the nanogel surface. This disclosure also provides methods of administering these nanogels to reduce the incidence of, or to treat, diseases and disorders in which an extended, sustained drug release is desirable, including bacterial infection of the bladder. These methods may include intravesicular administration of a nanogel of this disclosure to a subject in need of treatment for a disease or disorder of the bladder or urinary tract.

Nanogels (NG) are discrete nano-scale (5-100 nm) globular bundles of short polymer chains that are interconnected through covalent internal crosslinks and have the inherent ability to form a 3-dimensional cross-linked network. Each NG particle represents a single macromolecule that is densely interconnected to yield high molecular weight (105-107 kDa) NG particles. Because the NGs are initially formed in solution and then collapsed, the bulk nanogel structures can be readily swollen by and uniformly dispersed in monomer or in a solvent of an appropriate solubility parameter. The NGs can then be swollen up to 300% of their initial radius and designed to bear residual reactive sites that can be used to participate in secondary polymerizations. Forming photoreactive building blocks also permits the introduction of co-monomer mixtures that can maximize the drug loading capacity and encapsulation efficiency while retaining the ability to functionalize the nanogel with targeting entities (such as pentapeptide CGKRK (SEQ ID NO:1), which exhibits high cellular internalization via the transmembrane effect in an energy and heparan sulfate receptor-dependent manner).

Therefore, this disclosure provides highly specific, high-yield synthetic methodologies to yield polymeric nanoparticles with controlled average size, internal free volume hydrophilic/hydrophobic balance, and reactive group placement and concentration. The internal free volume of the nanogels can be altered by varying the effect of solvent to monomer ratio thereby controlling ability to uptake specific drugs while the chain transfer agent (CTA) concentration can significantly alter the crosslinking density and final structure of the NG. Depending on the co-monomers chosen to form the NGs, they can be formulated to encapsulate monomer or inert solvents to very high loading levels (≥80 wt %; similar volume fraction) to form to densely packed interdigitated structures.

Embodiments of the present invention described herein are related primarily to intravesical administration of an active pharmaceutical ingredient, but the invention is suitable for application of a nanogel or active pharmaceutical ingredient to any mucosal surface and/or epithelium of a mammal. By way of non-limiting example, embodiments of the present invention may be employed for administration of a nanogel and/or an active pharmaceutical ingredient to anal, bronchial, endometrial, esophageal, gastric, intestinal, lingual, nasal, olfactory, oral, penile, and vaginal mucosae, and to epithelial surfaces of the circulatory system (e.g. blood vessels), digestive system (e.g. submandibular glands, gingiva, tongue, esophagus, stomach, gallbladder, intestines, rectum, anus), endocrine system (e.g. thyroid follicles), lymphatic system (e.g. lymph vessels), integumentary system (e.g. skin, sweat glands), female and male reproductive systems (e.g. ovaries, Fallopian tubes, uterus, cervix, vagina, labia, testicular tubules, efferent and ejaculatory ducts, epididymis, vas deferens, bulbourethral glands, seminal vesicles), respiratory system (e.g. pharynx, larynx, trachea, bronchi and bronchioles, alveoli), sensory system (e.g. cornea, olfactory surfaces), and urinary system (e.g. kidneys, renal pelvis, ureter, urethra, bladder), of humans.

The nanogels of the present invention can be hydrophilic, hydrophobic, or amphiphilic (i.e. may comprise both hydrophobic and hydrophilic moieties). The nanogels may also carry a positive (cationic) or negative (anionic) electric charge, or may be uncharged. The relative hydrophilicity and/or hydrophobicity may be controlled by selecting appropriate monomers for use in the free radical solution polymerization and may be dictated by chemical and physical properties of the active pharmaceutical ingredient to be delivered, as will be understood by those of ordinary skill in the art.

Nanogels of this disclosure preferably comprise biodegradable and biocompatible natural or synthetic polymers that already have FDA approval, including synthetic polymers, such as polyglutamic acid and polyglycolic acid (PGA), poly(trimethylene carbonate) (PTMC), polyethylene glycol (PEG), polycaprolactone (PCL), polylactic acid (PLA), poly(D,L-lactide) (PDLLA), polyaspartate (PAA), poly(D,L-lactide-co-glycolic) acid (PLGA), and N-(2-hydroxypropyl)-methacrylamide copolymer (HPMA). These polymeric materials may be functionalized with methacrylate to produce methacrylate-functionalized macromers that are biodegradable synthetic hydrogels with good cell adhesion characteristics. These polymeric materials are easily manufactured and degraded after use, and produce a sustained release of the active compounds over time. However, natural polymers, such as chitosan, alginate, dextran, heparin, albumin, gelatin or collagen, are also non-toxic, abundant in nature, inexpensive, and easily biodegraded, providing relatively fast drug release profiles, and are therefore also useful in the nanogels of this disclosure. Preferably the polymeric monomers that compose the nanogels of this disclosure, when polymerized, form a polymer that is biocompatible and amenable to surface functionalization/photoactivation as described herein. Exemplary monomers for use in preparing the nanogels of this disclosure include hydroxyethyl acetate, ethylene glycol dimethacrylate, styrene, hydroxyethyl acrylate, and urethane dimethacrylate.

Similarly, though certain reaction times, temperatures, etc. are disclosed in the following Examples, those of ordinary skill in the art will understand that reaction conditions may be modified as appropriate for individual applications, and that such modifications are within the scope of the present invention. Particularly, while the embodiments of the invention described herein have utilized ultraviolet (UV) light for a period of about 10 to about 30 minutes to aggregate the photoactive nanogels, other wavelengths and exposure times may be suitable for particular applications, as will be understood by those of ordinary skill in the art, and are within the scope of the present invention. Similarly, any initiators, chain transfer agents, and other reagents appropriate for the chosen reaction conditions may be suitable for use in the present invention.

Nanogels and cell-penetrating peptides as disclosed herein are suitable to facilitate the delivery of any active pharmaceutical ingredient intended for application to any mucosal surface and/or epithelium of a mammal, and may be employed to treat any disease, disorder, or pathological condition of the mucosal surface and/or epithelium or any tissue associated therewith. By way of non-limiting example, the present invention may be suitable for delivery of anabolic steroids, analgesics, anesthetics, antibiotics, anticonvulsants, antidepressants, anti-inflammatories, antipsychotics, antivirals, anxiolytics, decongestants, estrogens and esters thereof, opioids, progestins, and testosterones and esters thereof. By way of further non-limiting example, the present invention may encompass methods suitable to treat behavioral disorders, diseases of the blood and blood-forming organs, diseases of the circulatory system, diseases of the digestive system, diseases of the ear and mastoid process, endocrine diseases, diseases of the eye and adnexa, diseases of the genitourinary system, diseases and disorders of the immune system, infectious and parasitic diseases, injuries, mental disorders, metabolic diseases, diseases of the musculoskeletal system and connective tissue, neoplasms, diseases of the nervous system, neurodevelopmental disorders, nutritional diseases, poisonings, diseases of the respiratory system, diseases of the skin and subcutaneous tissue, and diseases (including infections) of the urinary system.

Methods of the present invention may be practiced with any suitable cell-penetrating peptide, as will be understood by those of ordinary skill in the art. By way of non-limiting example, cell-penetrating peptides suitable for use in the present invention include the cell penetrating peptide CGKRK (SEQ ID NO:1), BMV Gag-(7-25), D-Tat, FBP, FHV Coat-(35-49), HTLV-II Rex-(4-16), MAP, MPG, MPG (ΔNLS), Penetratin, Pep-1, Pep-2, polyarginines, polylysines, PTD-4, PTD-5, R9-Tat, SBP, SynB1, SynB3, TAT, Transportan, and chimeras, combinations, and mixtures thereof. These cell-penetrating peptides may be covalently linked to the nanogel, in particular through methacrylate functional groups on the surface of the nanogel.

The nanogels of this disclosure may also be functionalized with cross-linkable double bonds. The cross-linking groups may comprise an ester group. After cross-linking in some embodiments, the linking groups may comprise at least two ester groups. In certain embodiments for biomedical applications, the hydrogel, cross-linked network, and/or the block copolymer comprising a nanogel includes a biocompatible linking group.

While various functional groups can be used to functionalize the co-polymers for cross-linking, in some embodiments the co-polymers are functionalized with methacrylate, diacryloyl or dimethacryloyl groups. For example, poloxamer diacrylate may be reacted with a dextran acrylate to form the hydrogel.

The co-polymers forming the nanogels of this disclosure may be cross-linked with any polymerization process or appropriate cross-linking reaction including radical polymerizations, emulsion polymerizations, controlled polymerization, UV initiated cross-linking, e-beam curing, or other polymerization processes.

The polymeric network may be cross-linked chemically or with ionizing radiation such as gamma or beta radiation.

The copolymer and/or hybrid polymer network may be produced from any desired ratio of monomers. For example, polyethylene glycol-styrene-hydroxyethyl acetate (PSH) nanogels are synthesized from hydrophilic monomer hydroxyethyl acetate (HEA), polyethylene glycol dimethacrylate, and hydrophobic monomer styrene. In an exemplary embodiment, a HEA:PEG:styrene molar ratio of 2:1:2 is used to form the PSH polymeric nanogel. Another example provides nanogels synthesized from 2-hydroxyethyl acrylate and urethane dimethacrylate (UDMA). In an exemplary embodiment, these nanogels were synthesized by a free radical solution polymerization using 85 mol % 2-hydroxyethyl acrylate and 15 mol % urethane dimethacrylate (UDMA).

The nanogels of this disclosure may be customized by adjusting various properties of the components comprising the nanogel and the processes used to produce the nanogel. For example, the degree of cross-linking will affect the properties of the hydrogel such as pore size. For example, in an e-beam cross-linking process, pore size can be adjusted during the irradiation/curing process by adjusting the strength or exposure time of the beam current. The monomers forming the nanogels, may also be polymerized through other chemical cross-linking methods, for example, peroxide, benzoyl peroxide, t-butyl peroxide, and hydrogen peroxide can produce free radicals and crosslink certain unsaturated polymers. The thermal initiator 2,2'-azobis(2-methylpropionitrile (AIBN) may be used in conjunction with chain transfer agents (CTA) such as 2-mercaptoethanol and mercaptosuccinic acid to polymerize the monomers. The monomers may also be polymerized via the application of ultra-violet light.

The nanogel production processes may have a significant effect on the rates of diffusion of the pharmaceuticals out of the nanogel. In some circumstances, it may be desirable to increase the elution rate of a given drug from the membrane.

The nanogels of this disclosure may comprise a nominal diameter between 1 nm and 1000 nm, or between 10 nm and 500 nm. For certain medicinal applications, embodiments of the nanogel may comprise a nominal diameter between 20 nm and 300 nm. In some embodiments, the hydrogel composition comprises nanoparticles in the range of from 20 to 250 nm in average diameter, or in the range of from 20 to 200 nm in average diameter, or in the range of from 50 to 120 nm in average diameter.

Surface conjugation of ligands to the nanogels of this disclosure, including but not limited to the pentapeptide CGKRK (SEQ ID NO:1), can be conducted by esterification, periodate oxidation, bromide activation, methacrylate functionalization, or acid-cleavable linking group.

This disclosure also provides methods for making a nanogel composition. For example, the method may comprise a thermally-initiated, solution polymerization that reacts a monovinyl monomer with a divinyl crosslinker in the presence of a chain transfer agent (CTA) such as 2-mercaptoethanol to obtain a cross-linked NG. The resulting NG can be functionalized via an alcohol-isocyanate reaction between the residual OH groups (introduced via the choice of monomer or CTA) and 2-isocyanoethyl methacrylate. Subsequently, the photoreactive NG conjugates with residual methacrylate functionality can be generated via a thiol-methacrylate Michael-Addition reaction.

The nanogels may encapsulate a therapeutic or diagnostic agent, such as but not limited to an antibiotic, a glucocorticoid, a monoclonal antibody, a polynucleotide, a peptide therapeutic, an enzyme, a hormone, or anti-inflammatory agent. In some embodiments, the therapeutic agent is an antibiotic such as, but not limited to gentamicin and/or ciprofloxacin. Alternatively, or additionally, the nanogels may incorporate a diagnostic agent, such as a fluorescently labelled agent (e.g., dye) or a radio labeled biomarker. A fluorescent or luminescent marker can be conjugated to the particles, or encapsulated by the particles, for diagnostic purposes (e.g., for detecting binding of nanoparticles to target cells or tissues), or for studying trafficking of the particles in vivo, for example. Examples include luciferin/luciferase biomarkers or GFP, as well as fluorescent dyes (e.g., AMCA), many of which are well known. Further, these markers can be encapsulated within the nanoparticles to study the kinetics and environments of biomarker release. The nanogels may comprise wound healing agents and the nanogel may allow for controlled release of the healing agents of the solution into the wound.

The hydrogels may comprise further additives. Some agents of therapeutic benefit include, but are not limited to, any type of antibiotic, gallium salts (gallium salts have been shown to kill *Pseudomonas Aeruginosa* and disrupt biofilm formation in wounds and particularly burn wounds), silver ions which are known to be bacteriostatic, metal chelators such as EDTA, transferrin, lactoferrin, siderophores, and/or other proteins such as proteins that bind iron may be bactericidal because bacteria require free iron for growth, chlorohexidine or any other type of antiseptic compound, cell wall hydrolytic enzymes, such as the phage-derived lysins or lysostaphin, or other enzymes capable of being bacteriolytic for select Gram-positive organisms, proteins such as dispersin B or glucuronidase which are capable of disrupting biofilm formation, bacteriocins or other proteins that perforate the outer membrane of Gram-negative organisms, bactericidal peptides, such as defensins, histatins, protegrins, tachyplesins, and thionins, quorum sensing inhibitors that disrupt bacterial signals when to change growth patterns or respond to external stress, fibrinogen, thrombin, and Factor 13 for formation of blood clots, growth factors, cytokines, or chemokines that are chemo-attractant for neutrophils and other immune cells.

In some aspects, this disclosure provides a method for treating or preventing a bacterial infection, comprising, administering a nanogel of this disclosure to a patient in need thereof. In particular, the invention finds use in treating bacterial infection of the bladder, or reducing the incidence or recurrence of urinary track infection, by instilling a nanogel of this disclosure into the urinary tract (typically through a catheter) to make contact with and adhere to the epithelial lining of the urinary tract and release a therapeutic entity (such as an antibiotic) over an extended period to the urinary tract. In these methods, the administration of the nanogel may be made by intravesical therapy (i.e., by instillation of the nanogel directly into the bladder via insertion of a urethral catheter). In these methods, the step of aggregating the loaded photoactive nanogel may be conducted in vivo by administering the loaded photoactive nanogel to the mammal and exposing the loaded photoactive nanogel to ultraviolet light to form an aggregated pharmaceutical nanogel in vivo. For example, the loaded photoactive nanogel may be administered intravesically followed by exposure to ultraviolet light provided into the bladder via a catheter, to form the aggregated pharmaceutical nanogel within the bladder of the mammal.

In other aspects, this disclosure provides methods of treating wounds, including deep cavity wounds, hospital acquired infections, surgical wounds, and burns. In some embodiments, the patient has an antibiotic resistant bacterial infection. In some embodiments, the nanogel is administered topically to the wound or infected region, or alternatively, is administered systemically, such as for patients showing signs or symptoms of sepsis or bacteremia, or at significant risk thereof.

In various embodiments, the nanogel compositions are administered to treat or prevent bacterial biofilm-associated urinary tract infections (UTI), sepsis, cellulitis and skin abscesses, pneumonia, toxic shock syndrome, or endocarditis.

The nanogel compositions may be administered to treat or prevent recurrent urinary tract infections (rUTI) including those resulting from uropathogenic *Escherichia coli* (UPEC), which establish biofilms within the urothelium, or *Pseudomonas aeruginosa* (PAO1) which forms highly resistant biofilms. The nanogel compositions may be administered to treat or prevent recurrent urinary tract infections (rUTI) in chronically-catheterized patients. Administration of the nanogels of this disclosure comprising an antibiotic may enable the antibiotic to penetrate the urothelium of the bladder to access biofilms urothelium to access intracellular biofilm reservoirs.

The nanogel compositions of this disclosure may be used to treat or prevent infection by a variety of bacterial pathogens, including drug-resistant pathogens. Examples of drug-resistant bacteria include: methicillin-resistant *Staphylococcus aureus* (MRSA), vancomycin-resistant *S. aureus* (VRSA), vancomycin-resistant *Enterococcus* (VRE), and multidrug-resistant *A. baumannii* (MRAB).

In these methods, the infection treated or prevented may be, for example, bacteremia, bacterial endocarditis, infections associated with external burns, infections associated with cystic fibrosis, prosthetic valve infections, native valve infection, infection associated with endometritis, infection associated with febrile neutropenia, infection associated with an in-dwelling medical device, intraabdominal infection, meningitis, infection associated with osteomyelitis, infection associated with pelvic inflammatory disease, infection associated with peritonitis, infections associated with pneumonia, infection associated with pyelonephritis, infection associated with skin or soft tissue, and infection associated with surgery.

These methods can be used for any one or more of the following purposes: alleviating one or more symptoms of a disease or disorder of the bladder (such as an infection or cancer of the bladder), delaying progression of a disease or disorder of the bladder, shrinking tumor size in a bladder cancer patient, inhibiting growth of an infectious organism or bladder cancer tumor growth, prolonging overall survival, prolonging disease-free survival, prolonging time to bladder disease progression, preventing or delaying bladder cancer metastasis, reducing (such as eradiating) preexisting bladder cancer metastasis or bladder cancer infections, reducing incidence or burden of preexisting bladder cancer metastasis, preventing recurrence of bladder cancer or bladder infections.

Routes of administration include topical administration, which may include topical application to the epithelial lining of the urinary tract such as the urothelium of the bladder (instillation directly into the bladder via insertion through a urethral catheter), intravenous administration, or by intramuscular, intraperitoneal, subcutaneous, intra-articular, intrasynovial, intrathecal, oral, or inhalation routes. In other embodiments, the nanogel compositions may be administered to infected eyes, ears, or sinus.

Other ligands can be incorporated into the hydrogel composition, other than antibiotics, to impart other targeting properties, such as targeting of mammalian tissues and cells, including cancer cells. For example, the nanoparticles may be functionalized with groups that are capable of binding with a receptor on a cell (e.g., a cancer cell) chemically attached to the nanogel or nanoparticle.

The nanogels of this disclosure can be non-biodegradable or biodegradable, bioabsorbable, and will deteriorate to elements naturally excreted or absorbed by the body allowing release of medicaments at the targeted site of administration. Exemplary polymeric hydrogels that are useful in the polymers and the methods of treatment of this disclosure include networks based on poly(trimethylene carbonate) (PTMC)-, poly(D,L-lactide)(PDLLA)-, poly(ε-caprolactone) (PCL)- and poly(ethylene glycol) (PEG) macromers. These polymers may be functionalized with methacrylate (dMA), which may in turn be linked to cell targeting molecules, such as the pentapeptide CGKRK (SEQ ID NO:1). Exemplary mixed-macromer hydrogel polymer networks prepared from combinations of PTMC-dMA, PDLLA-dMA, PCL-dMA, PEG-dMA, and PEG-dMA and hydrogel polymer networks prepared from PTMC-dMA, PDLLA, PEG-dMA, PTMC-dMA, and PEG-dMA form highly hydrophilic hydrogels that are useful in the polymers and the methods of treatment of this disclosure. Exemplary synthetic hydrogels that are useful in the polymers and the methods of treatment of this disclosure include hydrogels based on poly(vinyl alcohol) (PVA), poly(acrylamide) (PAA), poly(2-hydroxyethyl methacrylate) (PHEMA) and poly(ethylene glycol) (PEG), as well as amphiphilic copolymers of PEG with poly(ε-caprolactone) (PCL), poly(lactide-coglycolide), (PLGA), and poly(L-lactide) (PLLA). Thus, methacrylate-functionalized macromers based on poly (trimethylene carbonate) (PTMC), poly(D,L-lactide) (PDLLA), PCL, and PEG are particularly useful in in the polymers and the methods of treatment of this disclosure. These polymeric hydrogels are also particularly amenable to photopolymerization.

Targeting agents of the nanogels or nanoparticles are capable of binding to a receptor in the body. As used herein, a receptor is a molecule, or a portion of a molecule, found on the surface of a cell that receives chemical signals from substances outside the cell. Binding to the receptor may be through covalent bonding, ionic bonding, complexation, hydrogen bonding, dipole-dipole interaction, van der Waals forces or any combination of such associations between at least one site of the targeting agent and at least one site of the receptor, as long as the binding is sufficiently strong to essentially form a target-receptor associate. The targeting agent may be a monoclonal antibody or fragment, for example, or a soluble factor or natural ligand for the targeted receptor.

The following Examples demonstrate some of the various advantages, benefits, and principles of the present invention.

Example 1

Photoactive Nanogels for Intravesical Drug Delivery

Polyethylene glycol-styrene-hydroxyethyl acetate (PSH) nanogels were synthesized from hydrophilic monomer hydroxyethyl acetate (HEA), polyethylene glycol dimethacrylate having a molecular weight of 1,000 daltons (PEGDMA-1000), and hydrophobic monomer styrene in an HEA:PEG:styrene molar ratio of 2:1:2. The monomers were added to a round-bottom flask with a magnetic stirrer. 1 wt % of the thermal initiator azobisisobutyronitrile (AIBN) and 20 mol % of the chain transfer agent 2-mercaptoethanol were then added. Four separate samples of the monomer mixture were then dissolved in appropriate amounts of toluene to provide a solvent:monomer weight ratio of 2:1, 4:1, 6:1, and 8:1 in respective samples; the samples are respectively referred to as the "2×," "4×," "6×," and "8×" samples herein. Each reaction mixture was then stirred for four hours at 90° C. The reaction mixtures were precipitated via dropwise addition to a ten-fold excess of hexane; the precipitate was filtered and the residual solvent was removed under reduced pressure to isolate the nanogels. FIG. 1 illustrates the nanogel synthesis scheme.

The nanogels were then reacted with 2-isocyanatoethyl methacrylate (IEM) to impart methacrylate functional groups on the nanogel surface. 5 g of each nanogel was dissolved in 100 mL dichloromethane in a 250 mL round-bottom flask. 0.0039 mol of IEM and five drops (~25 mg) of dibutyltin diluarate (DBT) were added, and the flasks were stirred for 16 hours. After the reaction, the surface-modified nanogels were precipitated via dropwise addition to a tenfold excess of hexane; the precipitate was filtered and the residual solvent was removed under reduced pressure to isolate the methacrylated nanogels. These nanogels were then further purified via membrane dialysis against deionized water, with the water changed every two to three hours. After dialysis, the solution was lyophilized to obtain the methacrylated nanogels.

The infrared spectra between 400 and 4000 cm$^{-1}$ of the nanogels were obtained by Fourier transform infrared spectroscopy (FTIR) on a Nicolet iS50 FTIR instrument. The molecular weights of the nanogels were determined by gel permeation chromatography (GPC) on a Viscotek-270 dual detector, with tetrahydrofuran (0.35 mL/min) as the mobile phase and a column temperature of 35° C.; GPC calibration was based on a series of PMMA standards of known molecular weight and dispersity. The particle sizes and size distributions of the nanogels were determined by dynamic light scattering (DLS) using a Zetasizer NanoZS equipped with a helium-neon solid-state laser operating at 633 nm. The aggregation efficacy of the methacrylated nanogels were measured after 0 minutes, 10 minutes, 20 minutes, and 30 minutes of UV light exposure. All measurements, including zeta potential determination, were performed using 0.5 mg/mL aqueous solutions in glass cuvettes.

The nanogels were separately loaded with a rhodamine dye and fluorescein isothiocyanate (FITC)-dextran at a nanogel:dye weight ratio of 5:1. Each nanogel was suspended in 100 mL phosphate-buffered saline (PBS) at a concentration of 10 mg/mL, whereupon the appropriate amount of dye was added to the solution. The solutions were stirred overnight (~16 hours) to allow the dye to diffuse within the nanogel. Salt and free dye were removed by membrane dialysis against deionized water. The solutions were then lyophilized to obtain the dye-loaded nanogels. To study drug release kinetics, each dye-loaded nanogel was suspended in PBS at a concentration of 0.5 mg/mL and incubated at 37° C. The dye releases at 1 hour, 2 hours, 4 hours, 24 hours, 48 hours, 72 hours, 120 hours, and 168 hours of incubation were collected by ultracentrifugation and recorded using fluorescence spectroscopy. The release kinetics of the aggregated dye-loaded nanogel (see below) were similarly studied.

The cytocompatibility of the nanogel was evaluated by a direct contact test with a monolayer of L929 mouse fibroblast cells. L929 cells were sub-cultured from the stock culture by trypsinization and seeded into six-well tissue culture plates. Cells were fed with minimum essential medium (MEM) supplemented with fetal bovine serum, and were incubated with varying concentrations of nanogel at 37° C. in a 5% carbon dioxide atmosphere for 48 hours. The cell culture was examined microscopically for cellular response using a phase contrast inverted microscope. The morphology of the cells was assessed in comparison with a control.

FITC-labeled nanogel was diluted in PBS at various concentrations, e.g. 10 and 20 µg/mL, and added to collagen-coated 96-well plates. The plates were then exposed to UV light for 15 minutes, washed three times with 200 µL PBS, and imaged using a UV imager.

To study the effect of PSH nanogel for adhesion onto the bladder mucosal surface, nanogels were administered into the bladders of anesthetized female mice via the urethra. Each nanogel was tagged with fluorescent FITC dye in the backbone of the polymer network and IR 800 dye on the surface of the nanogel. 50 µL of a 10 mg/mL suspension of the 4× nanogel was introduced into the bladder intravesically and kept in the bladder for 15 minutes. The fluorescence of the completely filled bladder was imaged in situ using a fluorescence microscope. After 15 minutes of nanogel incubation, the mice were kept alive for 24 hours post-incubation. Fluorescent images of the bladder were taken after voiding and washing the bladder three times with PBS. The mice were then sacrificed and the bladder was dissected after washing a further three times with PBS. The dissected bladder was opened and imaged using a LI-COR scanner. The bladders from control mice (no nanogel treatment) were similarly imaged. Histology of the bladder sections was also analyzed to confirm the nanogel adhesion onto the bladder mucosae.

The average molecular weights, polydispersity indices, and hydrodynamic radii of the 2×, 4×, and 8× nanogels, estimated from the GPC results, are given in Table 1.

TABLE 1

Molecular weight, polydispersity, and hydrodynamic radii of nanogels, measured by GPC

| Sample ID | Molecular weight (Da) | Polydispersity index | Hydrodynamic radius (nm) |
|---|---|---|---|
| 2× | 80,000 | 1.8 | 4.4 |
| 4× | 28,000 | 1.4 | 3.0 |
| 8× | 2,600 | 2.3 | 1.3 |

As can be seen from Table 1, as the solvent:monomer ratio increases, the molecular weight of the nanogel decreases; thus, the molecular weight of the nanogel can be controlled by varying the mass of solvent. This effect may be attributed to the fact that as the monomer solution becomes more dilute, monomer molecules are, on average, farther apart, decreasing the likelihood of propagation of the polymer chain and enhancing the kinetics of the termination step.

The hydrodynamic radius and polydispersity indices of the 2×, 4×, and 8× nanogels, estimated from the DLS results, are given in Table 2.

TABLE 2

Polydispersity indices and hydrodynamic radii of nanogels, measured by DLS

| Sample ID | Hydrodynamic radius (nm) | Polydispersity index |
|---|---|---|
| 2× | 102.6 ± 12 | 0.18 |
| 4× | 76.6 ± 3.2 | 0.32 |
| 8× | 93.9 ± 4.5 | 0.23 |

The relatively greater hydrodynamic radius of the nanogels measured by DLS as compared to that measured by GPC is attributable to the fact that the hydrophilic nanogel swells to a greater extent in a polar solvent such as water (the DLS solvent) than in a non-polar solvent such as tetrahydrofuran (the GPC solvent).

The particle size, polydispersity index, and zeta potential of the 4× nanogel at various times during UV exposure are given in Table 3.

TABLE 3

Particle size, polydispersity indices, and zeta potential of nanogels

| UV exposure (min) | Particle size (nm) | Polydispersity index | Zeta potential (mV) |
|---|---|---|---|
| 0 | 76.66 ± 3.2 | 0.32 | −13.03 ± 1.58 |
| 10 | 167.1 ± 2.65 | 0.08 | |
| 20 | 220.73 ± 2.74 | 0.06 | |
| 30 | 238.6 ± 1.23 | 0.09 | −11.07 ± 0.21 |

As can be seen from Table 3, radical-initiated intermolecular reaction between nanogel molecules leads to an increase in aggregation with increasing UV exposure.

Figure 2:
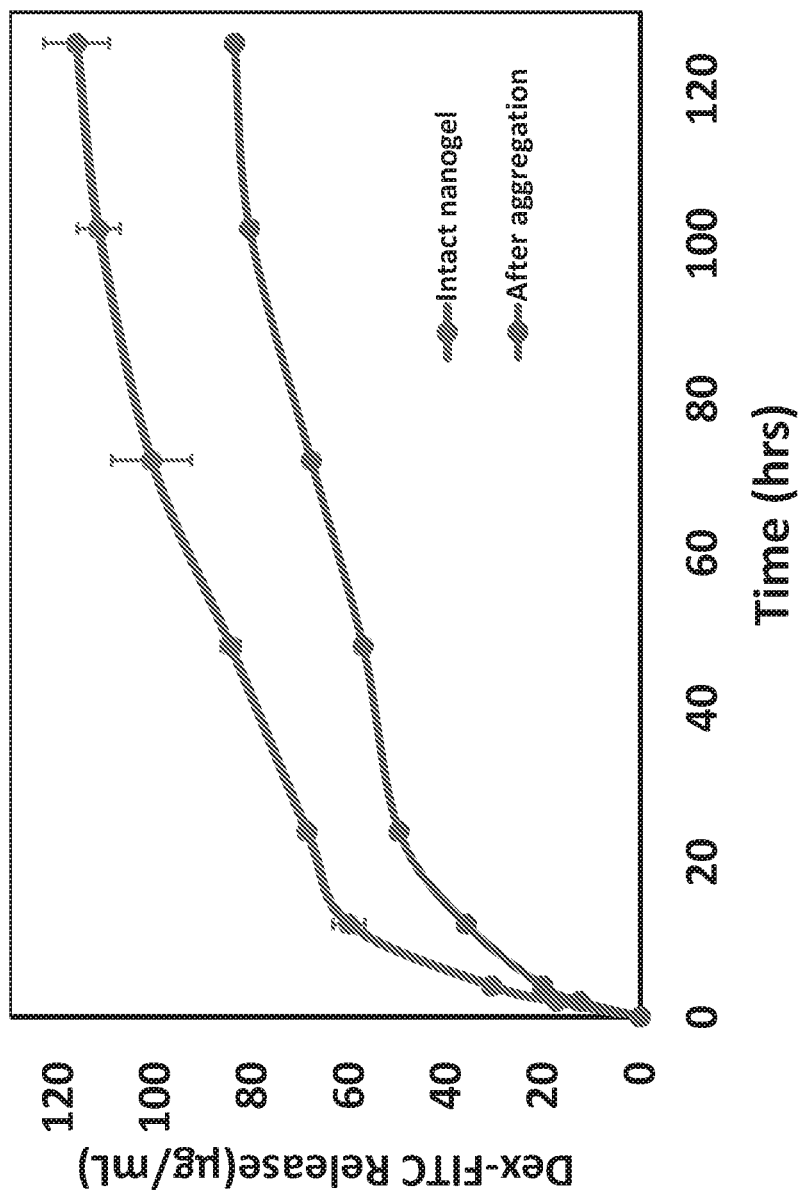
FIG. 2 is a graph of the release of FITC-dextran from nanogels of this disclosure over time.

Referring now to FIG. 2, release of the FITC-dextran is slower from the aggregated nanogel than from the unaggregated nanogel. In the aggregated nanogel, only 20% of the FITC-dextran is released as a "burst," 57% within 48 hours, and 83% within 120 hours. Thus, an extended release profile can be obtained by aggregation of the photoactive nanogel, which may be particularly effective for the treatment of, e.g., interstitial cystitis.

No change in the spindle morphology of mouse cells relative to the control was observed up to nanogel concentrations of 100 μg/mL. At concentrations of 200 μg/mL and above, cells begin to take on a spherical morphology, potentially indicating a mildly toxic effect of the nanogel at these concentrations.

Figure 3:
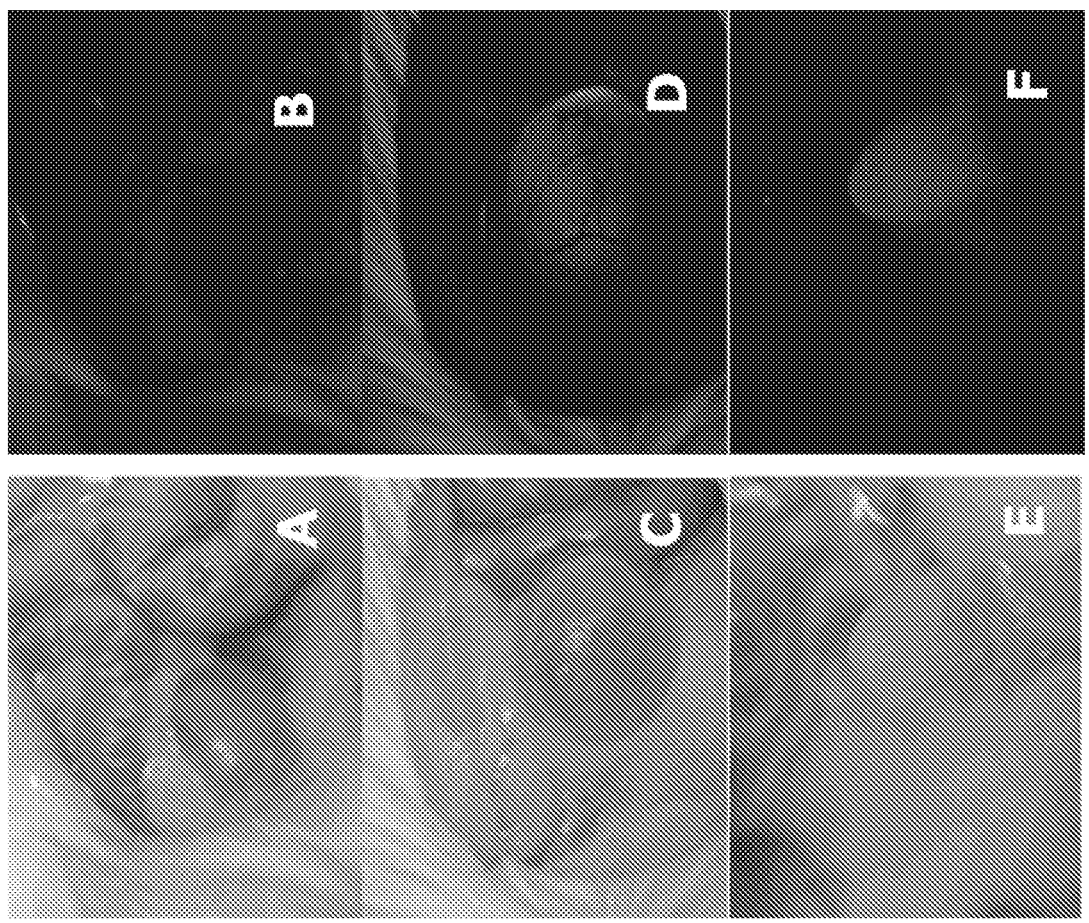
FIG. 3 depicts bright-field and fluorescence images of a mouse bladder from dye-tagged nanogel observed over 24 hours of incubation. Panels A and B bright-field and fluorescence images, respectively, after application; Panels C and D are bright-field and fluorescence images, respectively, of a nanogel-treated mouse bladder 2 hours post-incubation; Panels E and F are bright-field and fluorescence images, respectively, of a nanogel-treated mouse bladder 24 hours post-incubation.

Referring now to FIG. 3, a significant amount of fluorescence from the dye-tagged nanogel is observed even after 24 hours of incubation (compare the images of Panels A, C, and E; and the images of Panels B, D, and F; representing incubation times of 0 hours, 2 hours, and 24 hours). As the mice urinate frequently and non-adhered nanogel is thus very easily removed from the bladder, such strong fluorescence indicates strong adherence of the nanogel to the bladder mucosae. The present inventors hypothesize that the mucosal membrane may possess thiol functional groups derived from cysteine, and that methacrylate-functionalized nanogels may bind strongly to the bladder mucosae via thiol-ene-based esterification.

Figure 4:
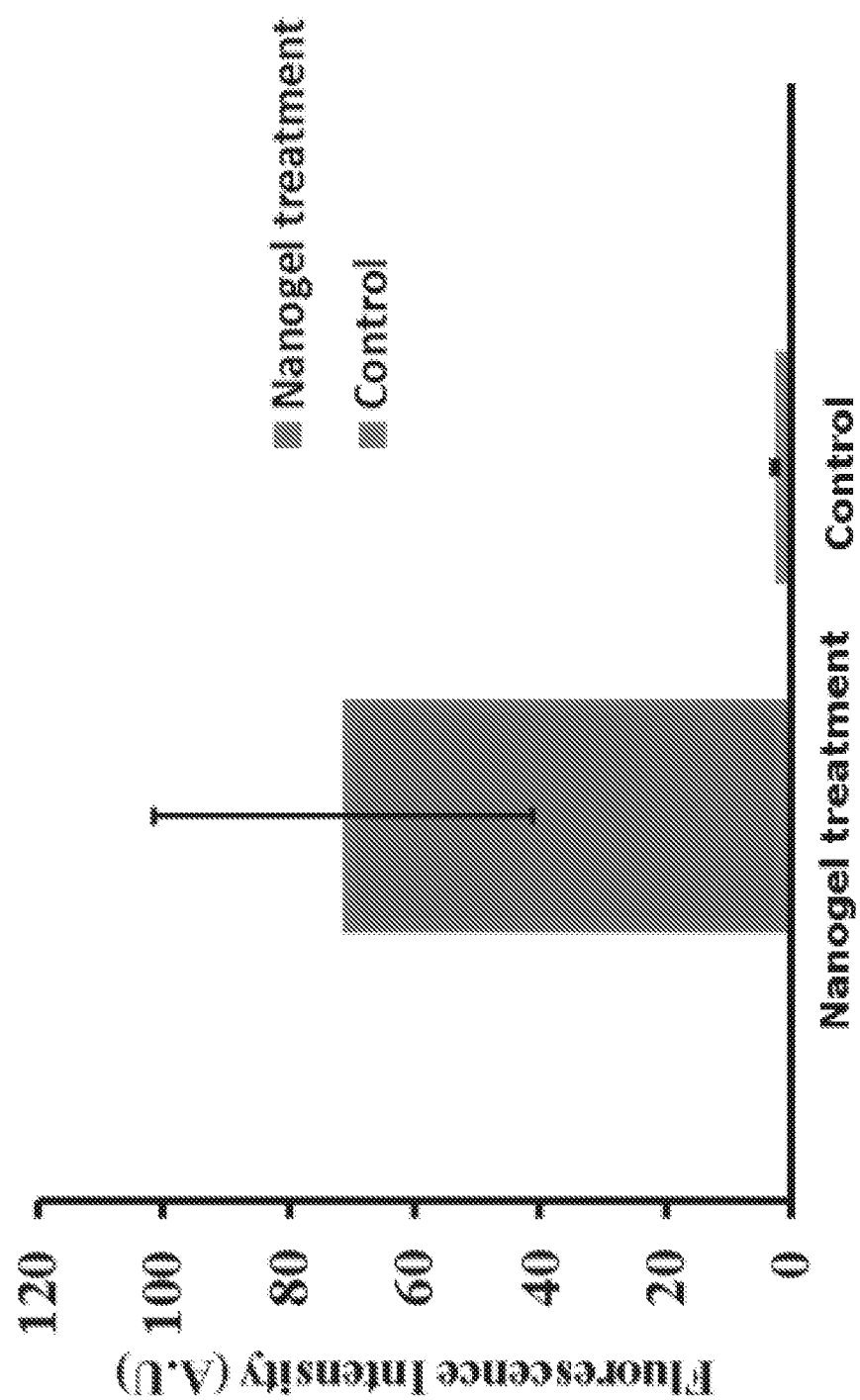
FIG. 4 is a graph of infrared intensity as a proxy for nanogel adhesion in the mouse bladders.

Referring now to FIG. 4, near-infrared (NIR) imaging and histological examination of the bladders reveals a significant accumulation of nanogel in the bladder lumen.

Example 2

Targeting of Bladder Mucosa by Cell-Penetrating Peptide CGKRK (SEQ ID NO:1)

Eight-to twelve-week-old female mice were anesthetized with isoflurane using a vaporizer machine at a flow rate of 1-3 L/min. The mice were placed on their backs and their urethra openings were pulled forward while squeezing the bladder to express urine. A lubricated 24 G Angiocath catheter with no needle was inserted via the urethra into the bladder cavity to wash the bladder once with 50 mL PBS. To imitate a bladder injury subsequent to bladder cancer surgery, in which the urothelium is damaged after the removal of cancer tissues, the catheter tip was inserted completely and five circular motions were made in the apical part of the bladder. A 1 mL syringe with 100 μL of a CGKRK peptide (SEQ ID NO:1) solution (0.3 mg/mL in 80% PBS/20% DMSO) was attached to the catheter, and approximately 50 μL of the solution was injected into the bladder until the bladder was completely distended, as determined by abdominal palpitation. The catheter with attached syringe was left in the bladder for 15 minutes. After incubation, the peptide was removed via negative pressure, and the bladder was washed 5 times with PBS, with complete filling of the bladder each time. A Dino-Lite AM4113T-GRFBY camera equipped with 480- and 570-nm excitation filters and 510- and 610-nm long pass emission filters was used to take images of the bladder in situ. The abdominal cavity was opened by incision, and the bladder was imaged at 20 to 40 times magnification. The images were acquired at 1280× 1024 resolution.

Freshly removed bladders were washed in PBS and snap frozen in liquid nitrogen. The tissue was embedded in optical cutting temperature (OCT) media and cryosectioned in consecutive 7-μm steps so that alternating sections were mounted on slides for fluorescence imaging and hematoxylin-eosin (H&E) staining, respectively. The tissues on each slide were fixed in a 10% buffered formalin solution, mounted with Vectashield™ antifade mounting medium with DAPI (for fluorescence imaging) or Permount™ medium (for H&E staining), and covered with a coverslip. The bladders imaged with a Nikon E600 upright fluorescence microscope with a SPOT RT color camera. The images in each fluorescence channel were acquired under saturation as 12-bit gray TIFF files, and H&E images were acquired as RGB images. Each low-magnification image covering the entire bladder area was analyzed with ImageJ software. The background was subtracted, and the integrated gray density per image was calculated. The intensities were plotted as individual values using Prism software.

The peptides CGKRK (SEQ ID NO:1) and KAREC (SEQ ID NO:2) were diluted two-fold in PBS at different concentrations and added to collagen- and heparin-coated wells preblocked with 5% bovine serum albumin. The plates were incubated at room temperature for 1 hour, washed 4 times with 200 μL PBS, and scanned at emission wavelengths of 485 and 515 nm using a SpectraMax M5 fluorescence plate reader. The PBS background was subtracted from the data points, and the data were plotted with Prism. The data were fitted into linear regression curves or non-linear saturation kinetics curves.

An MB49 bladder carcinoma cell line was maintained in full Dulbecco's modified Eagle's medium (DMEM) with antibiotics and L-glutamine. Cells were seeded on 24 well plates for at least 24 hours to allow the cells to grow to confluence; each sample was done in triplicate. Samples were then incubated with one of free CGKRK (SEQ ID NO:1) and KAREC (SEQ ID NO:2), micelles of these two peptides, fluorescence TAT peptide (positive control), and PBS (negative control). After the incubation, all wells were washed with PBS three times to remove any free fluorescence molecules. Cells were detached from the wells with trypsin at 37° C. for 5 minutes. 0.3% Triton X-100 in PBS was added to the cells, and after 30 minutes of incubation, the solutions were centrifugated in an Eppendorf microcentrifuge at 15,000 rpm. The fluorescence intensity of the supernatant was measured using a fluorescence plate reader. For confocal imaging, cells were grown on glass chamber slides. Following the incubation experiment, cells were imaged with a Nikon MR Confocal STORM super-resolution microscope.

Nanogels were synthesized by a free radical solution polymerization using 85 mol % 2-hydroxyethyl acrylate and 15 mol % urethane dimethacrylate (UDMA). 5.83 g of 2-hydroxyethyl acrylate and 4.17 g of UDMA were dissolved in 100 mL of a 1:1 toluene/methanol mixture in a 500 mL round-bottom flask. 1 wt % of AIBN, 10 mol % of 2-mercaptoethanol, and 10 mol % of the chain transfer agent mercaptosuccinic acid were added to the mixture, and the mixture was stirred at 85° C. for 3 hours. The reaction mixture was then precipitated via dropwise addition to a ten-fold excess (1 L) of hexane; the precipitate was filtered and the residual solvent was removed under reduced pressure to isolate the nanogel.

CGKRK peptide (SEQ ID NO:1) was conjugated onto the nanogel via a thiol-acrylate Michael addition reaction between the cysteine group on the peptide and the acrylate functionality on the nanogel, with triethylamine as the catalyst. 13 mg of nanogel was dispersed in 10 mL of PBS with 5 wt % DMSO. To this mixture, 100 µL of 10 mM CGKRK peptide (SEQ ID NO:1) stock solution and 50 µL of triethylamine were added, and the mixture was stirred at ambient temperature (approx. 22° C.) for 16 hours. 100 µL of 2-mercaptoethanol was added to the reaction mixture to consume any unreacted acrylate groups within the nanogel. The reaction mixture was then purified by membrane dialysis against deionized water for 48 hours and subsequently lyophilized to obtain the CGKRK (SEQ ID NO:1)-loaded nanogel. For Rhodamine B loading, 10 mg of CGKRK (SEQ ID NO:1)-loaded nanogel was dispersed in 6 mL of PBS with 20 wt % DMSO and 2 mg Rhodamine B in a 50 mL round-bottom flask and stirred at ambient temperature (~22° C.) for 16 hours. The reaction mixture was then purified by membrane dialysis against deionized water for 48 hours and subsequently lyophilized to obtain the Rhodamine B-loaded nanogel. A similar procedure was used to load Rhoadmine B onto nanogels without the peptide for use as a control for subsequent animal studies.

The conversion of the (meth)acrylate during the nanogel synthesis was quantified by FTIR between 400 and 400 $cm^{-1}$, and specifically at the characteristic (meth)acrylate group wavelength of 814 $cm^{-1}$, on a Nicolet iS50 FTIR instrument. The reaction was terminated once 85% conversion was attained so that (meth)acrylate functionality would be retained and available to facilitate subsequent CGKRK (SEQ ID NO:1) conjugation via the thiol-acrylate Michael addition reaction. The molecular weight of the nanogel, as determined by triple-detection GPC, was 13.5 kDa. The particle sizes and size distributions of the nanogels were determined by DLS using a Zetasizer NanoZS instrument; the average hydrodynamic diameter was 43.25±1.15 nm. All size measurements, were performed using 0.5 mg/mL aqueous solutions in glass cuvettes. The zeta potential across the nanogel dispersion at a concentration of 5 mg/mL in an aqueous 5 wt % DMSO solvent was observed to be −23.34±0.034 mV.

Figure 8A:
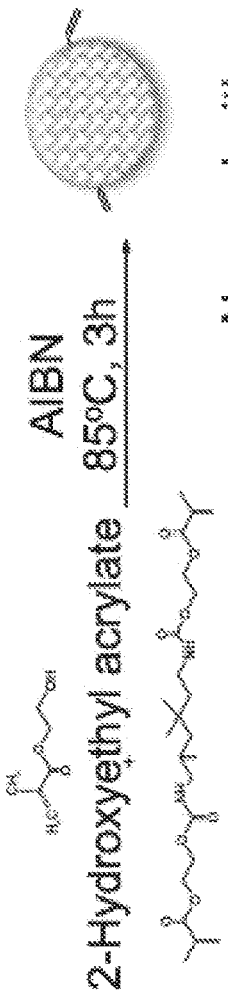
FIGS. 8A through 8F illustrate targeting of nanogel-loaded Rhodamine to a bladder.
Figure 8A:
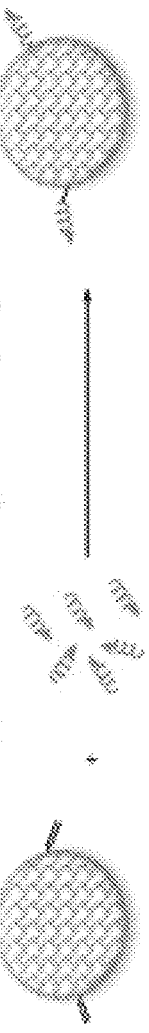
Figure 8A:
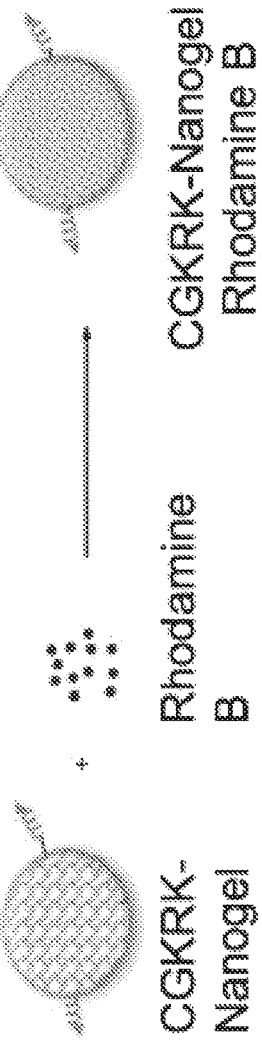

2 mg of the rhodamine-loaded nanogel was dispersed in 4 mL of PBS with 0.5 wt % DMSO and incubated at 37° C. The rhodamine release from the nanogels was quantified at incubation times of 1 hour, 2 hours, 4 hours, 6 hours, and 24 hours by measuring the fluorescence intensity at 625 nm (excitation wavelength 524 nm) using a microplate reader; each data point represents the average of three observations. The syntheses of the nanogel, CGKRK (SEQ ID NO:1)-loaded nanogel, and rhodamine-loaded nanogel are illustrated in FIG. 8A.

Referring now to FIGS. 5A through 5C, the cell and stroma binding properties of CGKRK (SEQ ID NO:1) are illustrated. Confocal microscope images of cellular uptake of peptides following incubation with MB49 bladder carcinoma cells indicate significant accumulation of CGKRK (SEQ ID NO:1), but not KAREC (SEQ ID NO:2), in the cytoplasm of the cells. Quantification of the peptide uptake by fluorescence spectroscopy (FIG. 5A) shows significantly more accumulation of CGKRK (SEQ ID NO:1) than of KAREC (SEQ ID NO:2) in the cells. The graphs illustrating binding to heparin (FIG. 5B) and collagen type I (FIG. 5C) of CGKRK (SEQ ID NO:1) (solid line) and KAREC (SEQ ID NO:2) (dotted line) show saturation kinetics of CGKRK (SEQ ID NO:1) binding to collagen and linear kinetics for other binding. Taken collectively, then, these data illustrate that CGKRK (SEQ ID NO:1) shows more efficient binding to both heparin and collagen type I, which are the major components of the bladder matrix and bladder mucosae.

Figures 6A, 6B:
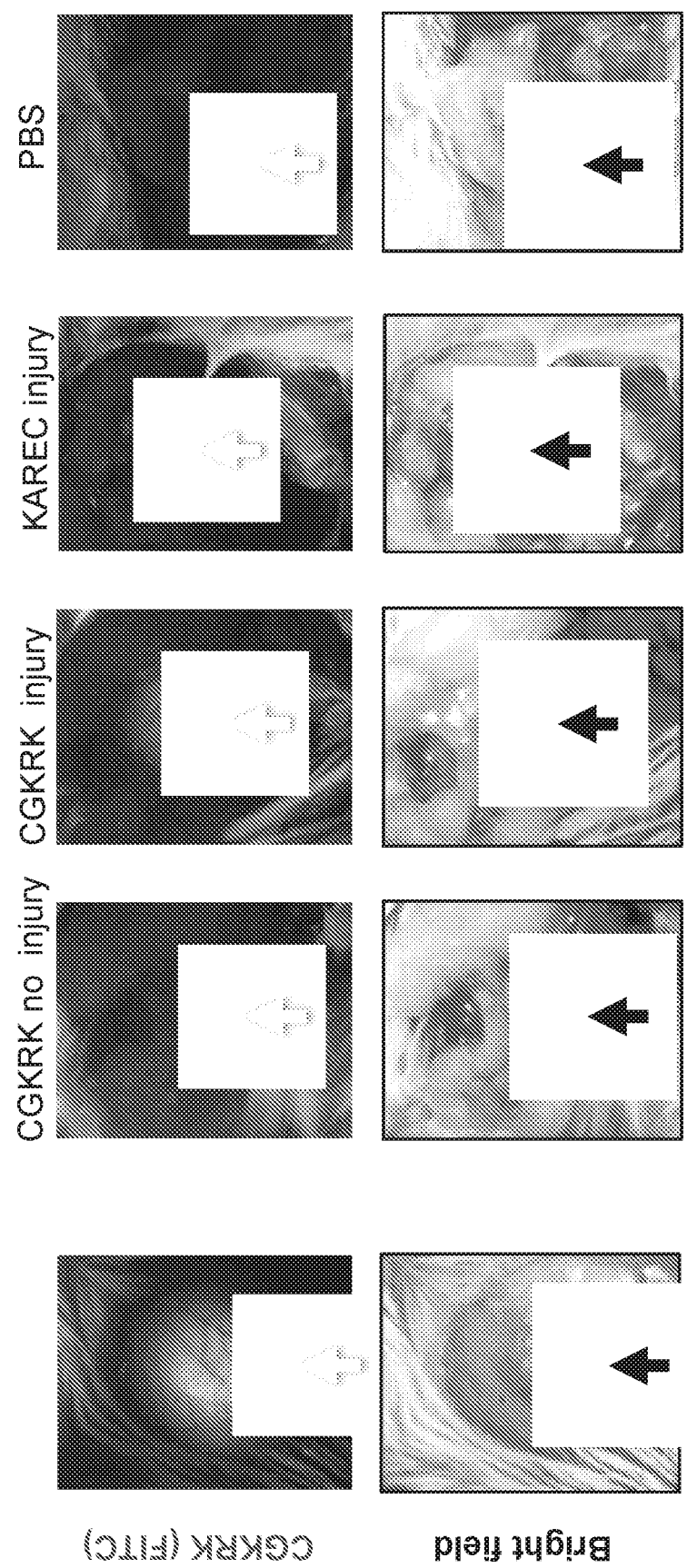
FIGS. 6A and 6B illustrate the effect of mechanical injury on accumulation of peptides in the bladder.

Referring now to FIGS. 6A and 6B, the effect of mechanical injury on accumulation of peptides in the bladder is illustrated. Mice were treated by washing the bladder and inducing injury to the mucosal surface of the bladder; the peptide was then injected into the bladder and incubated 15 minutes; the bladder was then washed 5 times. The fluorescence (top) and bright field (bottom) in situ images of the bladders (FIGS. 6A and 6B) show no binding of CGKRK (SEQ ID NO:1) in the absence of focal injury, but efficient binding after injury. KAREC (SEQ ID NO:2) showed limited binding at the injury site, and there was no fluorescence in the bladders treated with PBS (the control). The arrows in FIGS. 6A and 6B indicate the apical region of the bladder.

Figure 7:
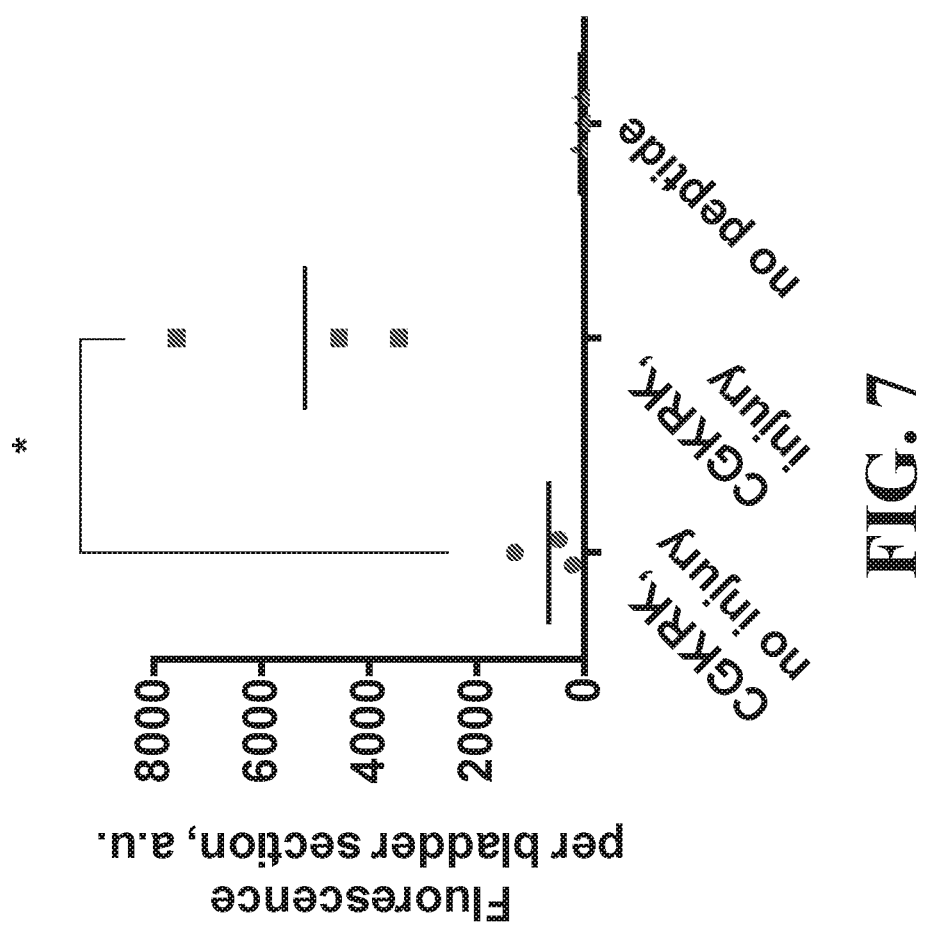
FIG. 7 illustrates histological analysis of peptide binding to the urothelium.

Referring now to FIG. 7, histological analyses of peptide binding to the urothelium is illustrated. 2× magnification of fluorescence and H&E stained images of the entire bladder treated with CGKRK (SEQ ID NO:1) showed widespread binding of CGKRK (SEQ ID NO:1) in the vicinity of the lumen. At 20× magnification, accumulation of the peptide in the urothelium (U) and some penetration into the muscle layer (ML) is revealed. FIG. 7 illustrates ImageJ quantification of FITC intensity in the bladder. 2× magnification fluorescence and H&E stain images of the entire bladder treated with KAREC (SEQ ID NO:2) showed less efficient and less widespread accumulation.

An investigation of the mechanisms of injury-induced accumulation of CGKRK (SEQ ID NO:1) was conducted. CGKRK (SEQ ID NO:1) was mixed with EDTA-treated blood and administered intravesically. 10×-magnification showed the lumen, the urothelium, and the muscle layer. Blood did not induce binding in the absence of injury suggesting that bleeding caused by the injury per se is not responsible for widespread binding. Mice were pretreated with the anti-inflammatory agent dexamethasone prior to injury. This pretreatment did not block injury-induced binding of CGKRK (SEQ ID NO:1). Chemical disruption of the urothelium barrier with ethanol resulted in widespread accumulation of CGKRK (SEQ ID NO:1) that could be observed at both 2× and 20× magnification, suggesting that loss of the barrier function is a requirement for CGKRK (SEQ ID NO:1) binding.

Figure 8B:
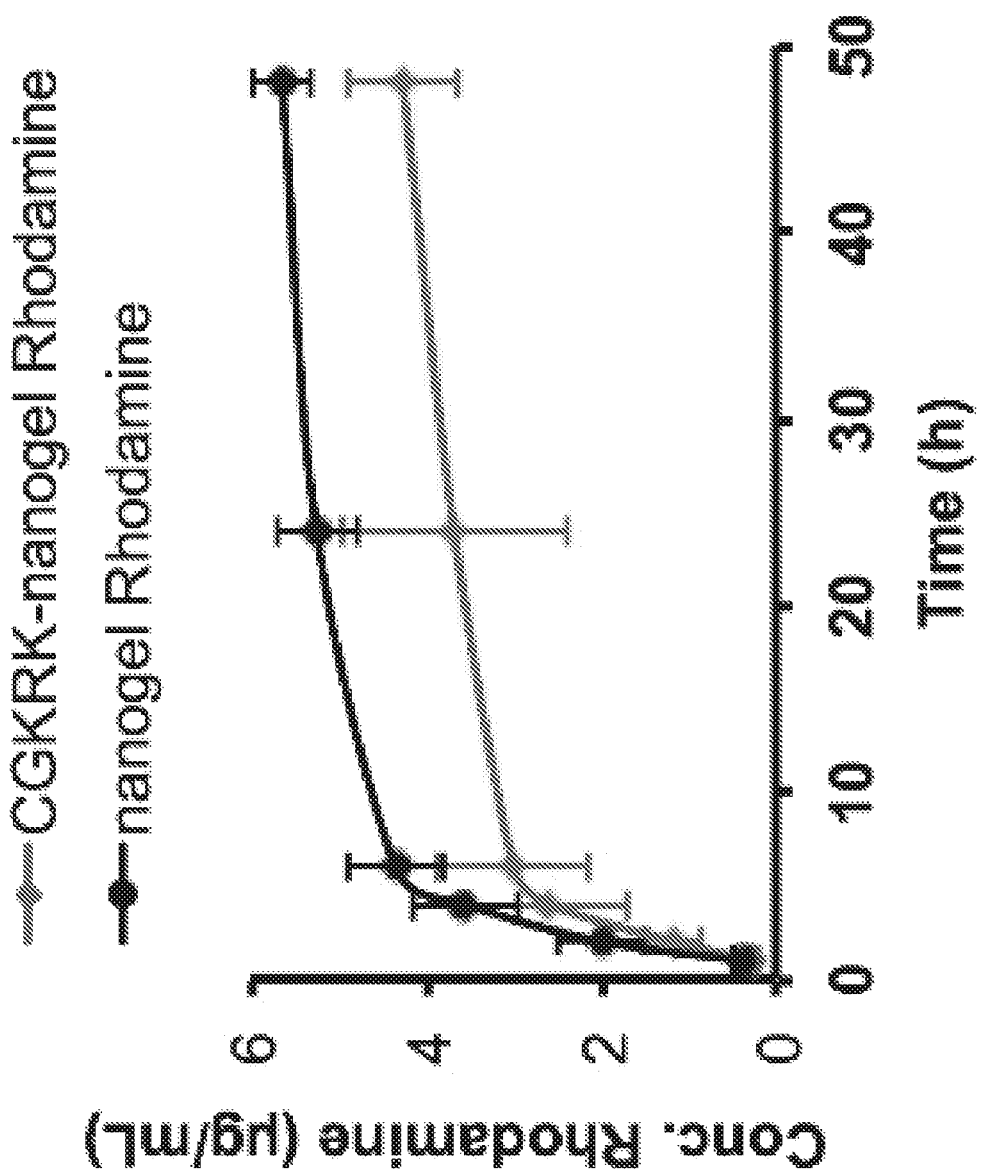
Figure 8C:
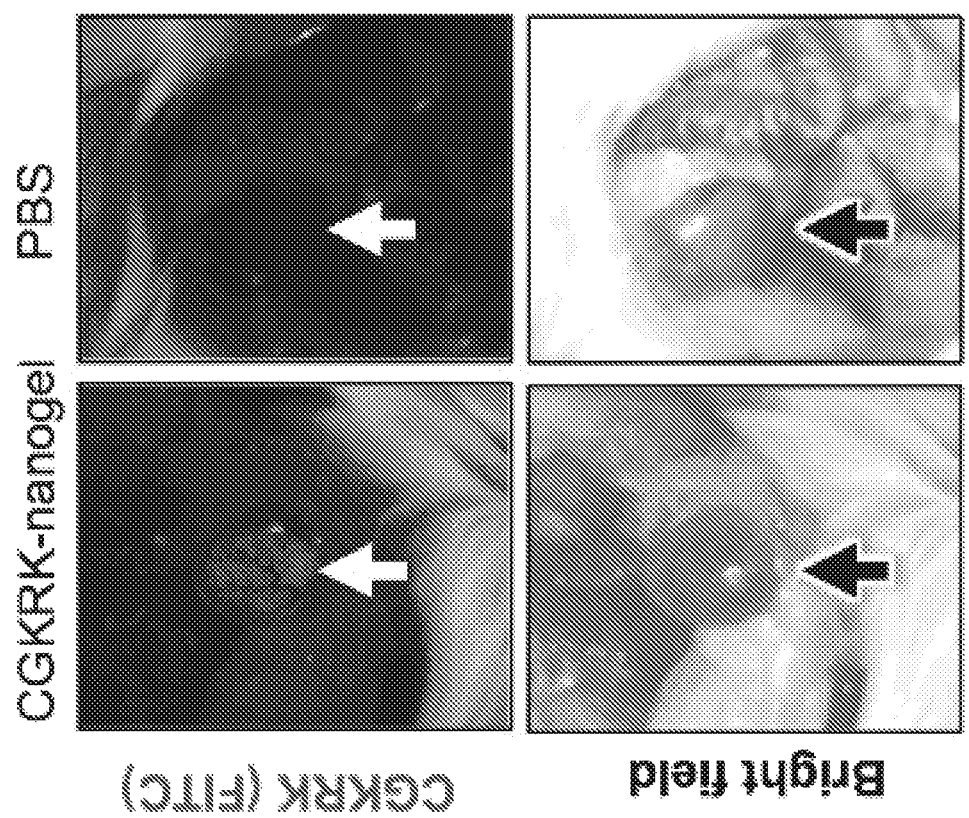
Figure 8D:
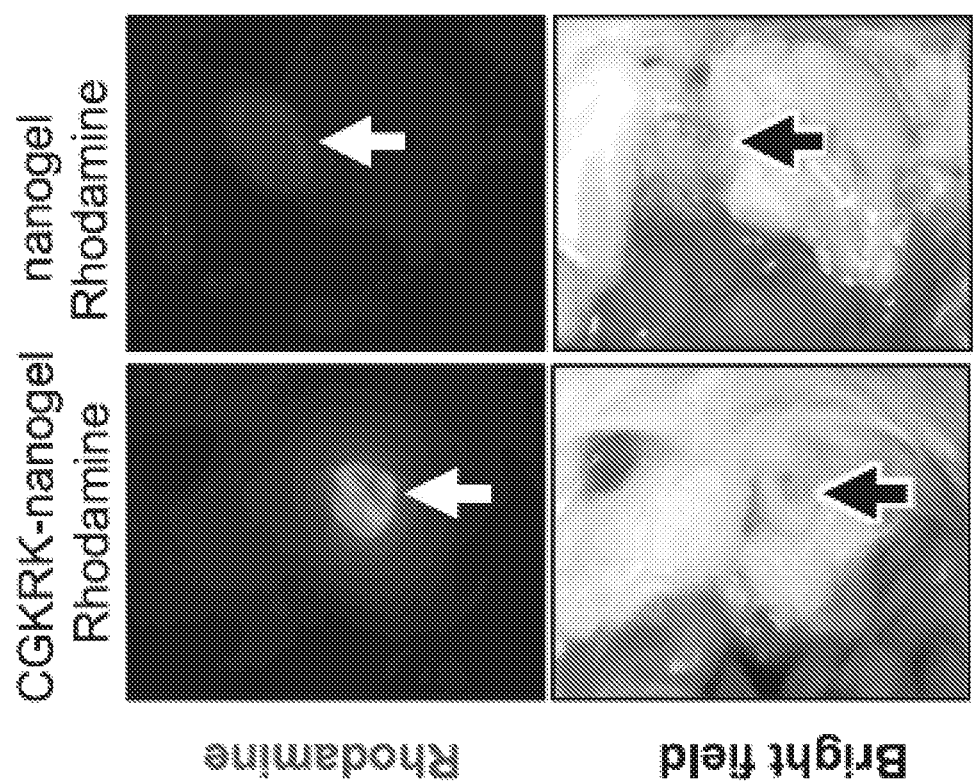
Figure 8E:
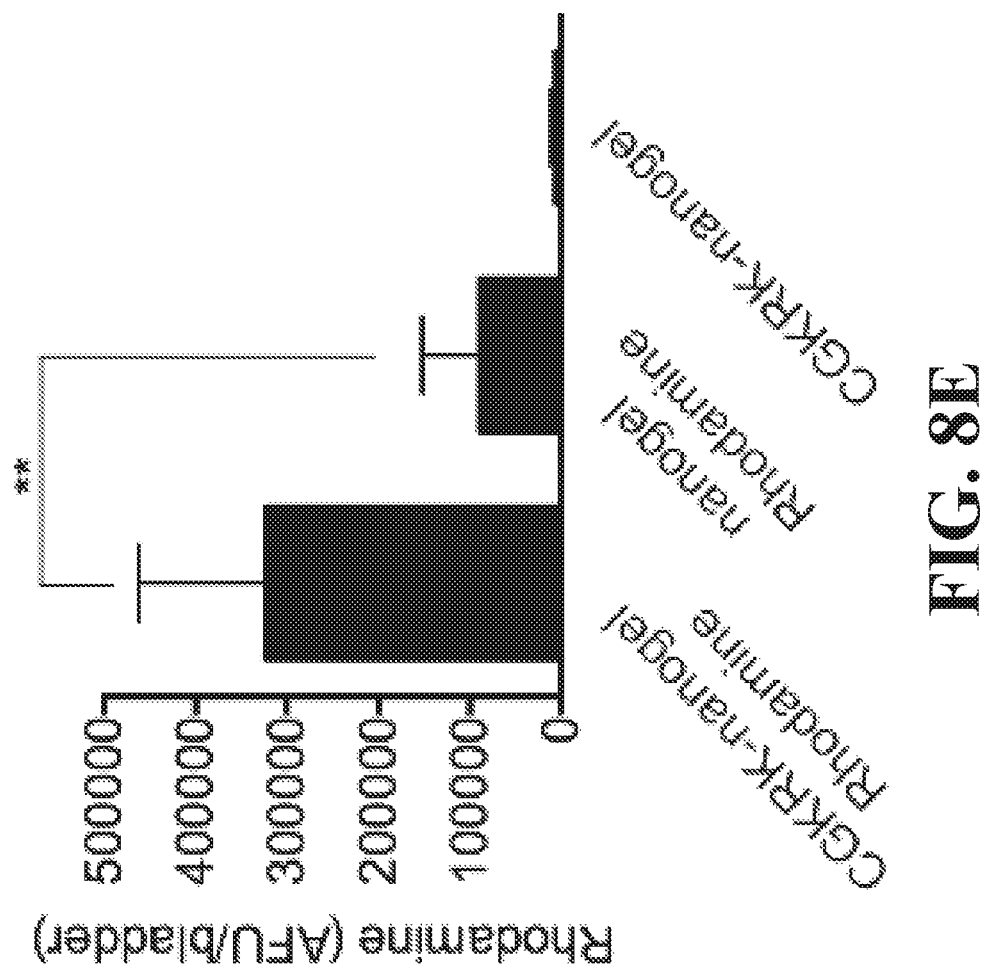
Figure 8F:
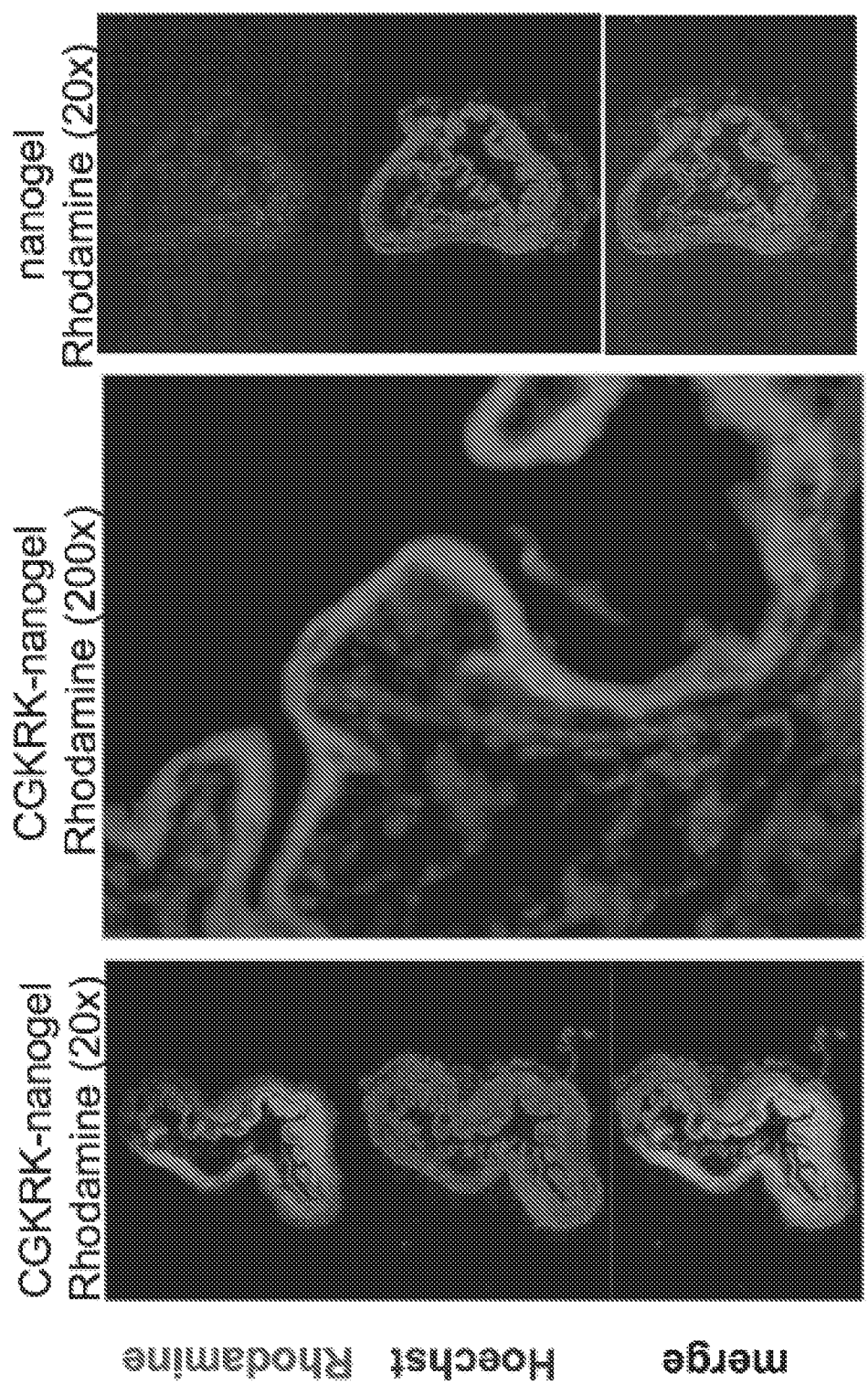

Referring now to FIGS. 8A through 8F, targeting of the Rhodamine B-loaded nanogel to the bladder is illustrated. FIG. 8A depicts the synthesis procedure used to produce the nanogel linked to the CGKRK (SEQ ID NO:1) peptide comprising ("loaded" with) rhodamine B. FIG. 8B illustrates the release profiles of Rhodamine B from both CGKRK (SEQ ID NO:1)-loaded and non-CGKRK (SEQ ID NO:1)-loaded nanogels and shows that release of the Rhodamine B is slightly faster in the non-loaded nanogel. FIG. 8C illustrates that administration of CGKRK (SEQ ID NO:1)-loaded nanogel without Rhodamine B to the injured bladder results in FITC accumulation (indicated by the arrow). FIG. 8D illustrates that administration of Rhodamine B-loaded nanogel to the injured bladder results in Rhodamine B fluorescence for CGKRK (SEQ ID NO:1)-loaded nanogel, but not for non-CGKRK (SEQ ID NO:1)-loaded nanogel. FIG. 8E illustrates that quantification of Rhodamine B fluorescence showed significantly higher accumulation for the CGKRK (SEQ ID NO:1)-loaded Rhodamine B nanogel. FIG. 8F illustrates histological sections of the nanogel-treated bladders and shows widespread accumulation of Rhodamine fluorescence in the bladder treated with CGKRK (SEQ ID NO:1)-loaded nanogel, but not in the bladder treated with non-CGKRK (SEQ ID NO:1)-loaded nanogel.

Example 3

Nanogel Synthesis and Drug Encapsulation

Two nanogels (NGs) were synthesized following the protocol depicted in FIG. 1 in which monomers with a history of biocompatibility were utilized to create the networks. The methacrylate functionality covalently tethered onto the surface of the NGs was utilized for post polymerization modification via conjugation with the CGKRK peptide (SEQ ID NO:1) via a thiol-Michael addition reaction, followed by photo-induced crosslinking/nanogel aggregation in the presence of a photoinitiator and light.

The co-monomers in the first nanogel (NG 1) were 2-hydroxyethyl acrylate and urethane dimethacrylate in 85:15 molar ratio while the second nanogel (NG2) was synthesized with 2-hydroxyethyl acrylate, acrylic acid, and tetraethylene glycol dimethacrylate in 60:20:20 molar ratio. For the synthesis of the NGs, the thermal initiator 2,2'-azobis (2-methylpropionitrile (AIBN-1 wt. %), and chain transfer agents (CTA) 2-mercaptoethanol (10 mol %) and mercaptosuccinic acid (10 mol %) were added to a mixture of solvents at a ratio of 1:1, toluene/methanol in a 500 mL round bottom flask and stirred at 85° C. for 3 h. The reaction mixture was then precipitated via drop-wise addition to a ten-fold excess of hexane (1 L). The precipitate was filtered and the residual solvent removed under reduced pressure to isolate the nanogel. Fourier Transform Infrared Spectroscopy (FTIR, 400 and 4000 cm-1, in mid-IR) was used to quantify the conversion of the methacrylate during the nanogel synthesis by monitoring the methacrylate group at 814 cm-1. The resulting NGs were characterized by triple detector Gas Permeation Chromatography (for molecular weight, polydispersity, hydrodynamic radius), and NMR (for composition and residual polymerizable methacrylate concentration) and cytocompatibility. A comparison of the hydrodynamic radius of the NGs in two different solvents (THF and PBS solution) demonstrate the ability of the nanogel to swell and collapse as a function of solvent is in Table 4.

TABLE 4

The molecular weight and radius of NGs synthesized. The hydrodynamic radius varies as a function of the solvent the NGs are dispersed in.

| Nanogels (NGs) | Mw (via GPC) | Rh (THF) | Rh (PBS) |
|---|---|---|---|
| NG1 | 13.5 kDa | 5 nm | 22 nm |
| NG2 | 42.7 kDa | 7 nm | 149 nm |

It is this ability of the NGs to swell up to 20 times their initial radius (NG2) that makes the NG an efficient drug reservoir and delivery mechanism. The data also indicates that this approach allows for blended mixtures of hydrophilic and hydrophobic nanogels as well as amphiphilic nanogels to be used to create tailored networks and/or even carry a multi-drug cocktail to the targeted site. The CGKRK peptide (SEQ ID NO:1) was conjugated onto the NGs via a thiol-methacrylate Michael addition reaction between the cysteine group on the peptide and the methacrylate functionality on the NG with triethylamine as the catalyst (FIG. 1). The reaction proceeded under ambient conditions (22° C.) for 16 h in PBS with 5 wt % DMSO. The reaction mixture was then dialyzed (MWCO; 3.5 KDa) against deionized water for 48 h and subsequently freeze-dried to obtain the NG in which approximately two peptides per polymer chain were reacted. The cytocompatibility of the CGKRK (SEQ ID NO:1)-NGs were evaluated by the direct contact test with a monolayer of L929 mouse fibroblast cells according to ISO standards (ISO 10993-5, 1999). Briefly, L929 cells were sub-cultured from the stock culture by trypsinization and seeded into 24 well tissue culture plates. Cells were incubated with different concentration of nanogel at 37° C. for 48 h while fed with minimum essential medium (MEM) supplemented with fetal bovine serum. Cells were examined microscopically for cellular response using a phase contrast inverted microscope. The morphology of the cells assessed in comparison with a control (media only) and the viable and non-viable non-adherent cells were counted using a standard hemocytometer. CGKRK (SEQ ID NO:1) linked NG1 was found to be non-toxic up to a concentration of 100 μg/ml whereas the more hydrophilic CGKRK (SEQ ID NO:1) linked NG2 was cytocompatible up to 250 μg/ml.

To encapsulate Rhodamine B as a drug mimic within NG1, 10 ml was dispersed in 6 mL PBS with 20% DMSO along with 2 mg Rhodamine B in a 50-mL round bottom flask and stirred under ambient conditions (22° C.) for 16 h. The mixture was dialyzed (MWCO; 3.5 KDa) against deionized water for 48 h and then freeze dried to obtain the Rhodamine B-loaded NGs. The Rhodamine B released from the nanogels were quantified at regular time intervals (1 h, 2 h, 4 h, 6 h, 24 h and 48 h) by measuring the fluorescence intensity at 625 nm (excitation wavelength 524 nm) using a microplate reader. The encapsulation efficiency and drug loading capacity was calculated to be at 10% and 4.6% while only 18% of the Rhodamine B was released from NG1 within 48 h, indicating that both the drug loading capacity and release rates from the NG1 can be optimized. These results demonstrate that the synthesized NGs can encapsulate and deliver drugs in a sustained manner.

Example 4

Nanogel Binding to Urothelium

Figure 9A:
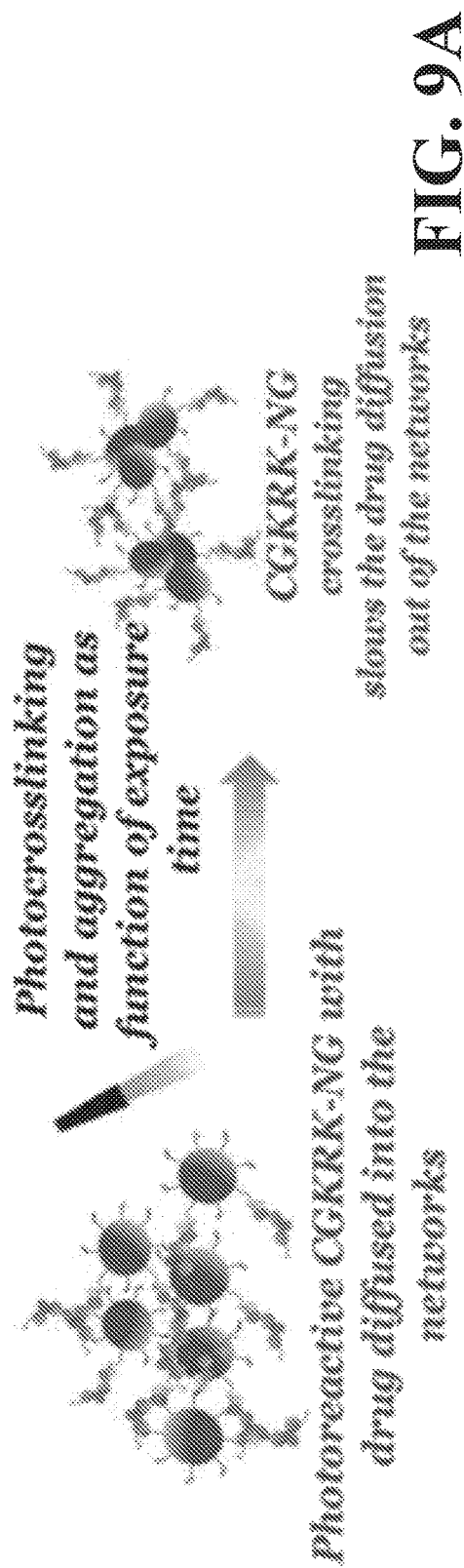
FIGS. 9A and 9B illustrate the release of FITC from nanogels of this disclosure.
Figure 9B:
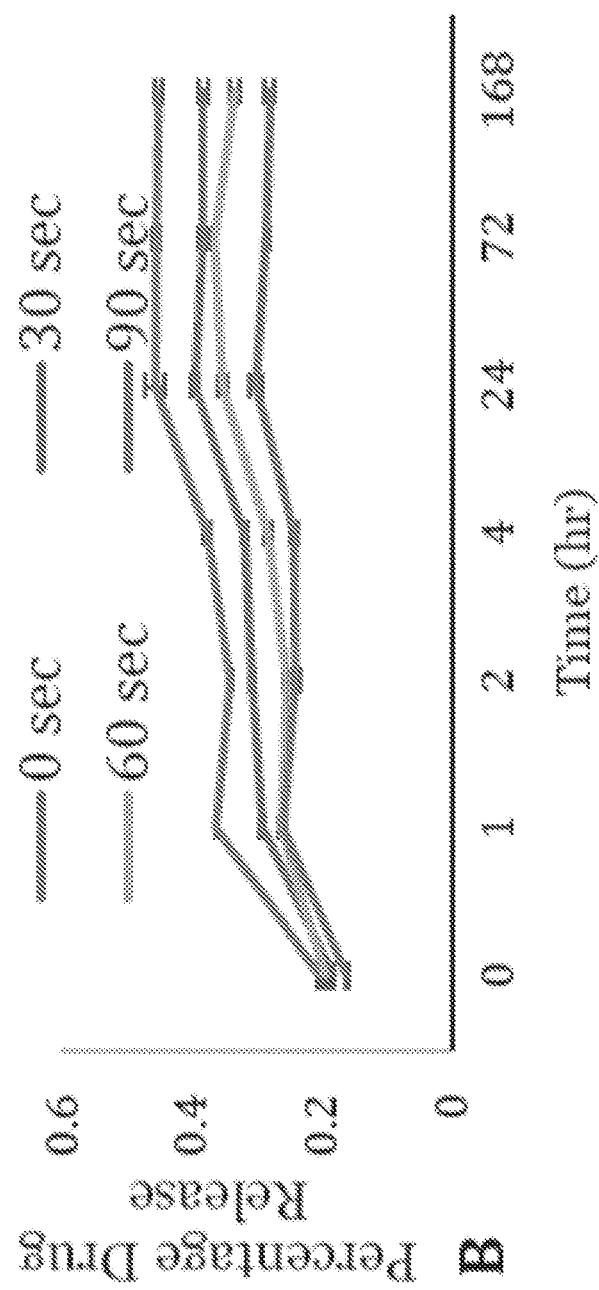

In-vivo experiments also indicated that the CGKRK (SEQ ID NO:1)-NG1 conjugates can bind and penetrate the mouse urothelium. CGKRK (SEQ ID NO:1)-NG1 loaded with Rhodamine B as a drug mimic was delivered via lubricated 24 G Angiocath catheter without the needle and inserted via the urethra into the bladder cavity of three 8-12 week female mice (C57BL/6 or BALB/c). Three circular motions were made on the cell layer via the catheter tip at the time of delivery to introduce injury on the bladder wall. Histological examination of the bladders revealed an intense accumulation of Rhodamine B (NG1) in the entire bladder lumen, with some fluorescence penetrating beyond the mucosal layer whereas non-targeted NGs showed minimal signal in the bladder. The bladders were imaged with a Nikon E600 upright fluorescence microscope with SPOT RT color camera. Prior to instillation of the NGs in the bladder, it is possible to curb the burst release kinetics and control the release rate of a drug in a facile manner via short exposures of the photoreactive, methacrylate-functionalized NG2 to UV wavelengths at 365 nm (FIG. 9A). The fluorescent drug mimic FITC was utilized to demonstrate that brief exposure to (30, 60, and 90 s at 7 mW/cm1 light) 365 nm UV light can significantly alter the drug release kinetics of the NGs, curb the burst release from the NGs and enable the sustained release of the FITC from the NG (FIG. 9B). The difference in FITC release rate is achieved via a UV-induced cross-linking that reduces the mesh size on the surface of the NG, thereby altering the release kinetics from the NG. These results demonstrate advantages of the formulated NG networks as drug delivery networks.

Example 5

High-Yield Methodologies to Generate Reactive NGs with Higher Drug Loading Capacity To better enable the one-time delivery of an antibiotic via a bladder installation procedure, the drug loading capacity of the NGs has to increase and the ability of the NG to release the antibiotics in a sustained manner has to be optimized.

Figure 10:
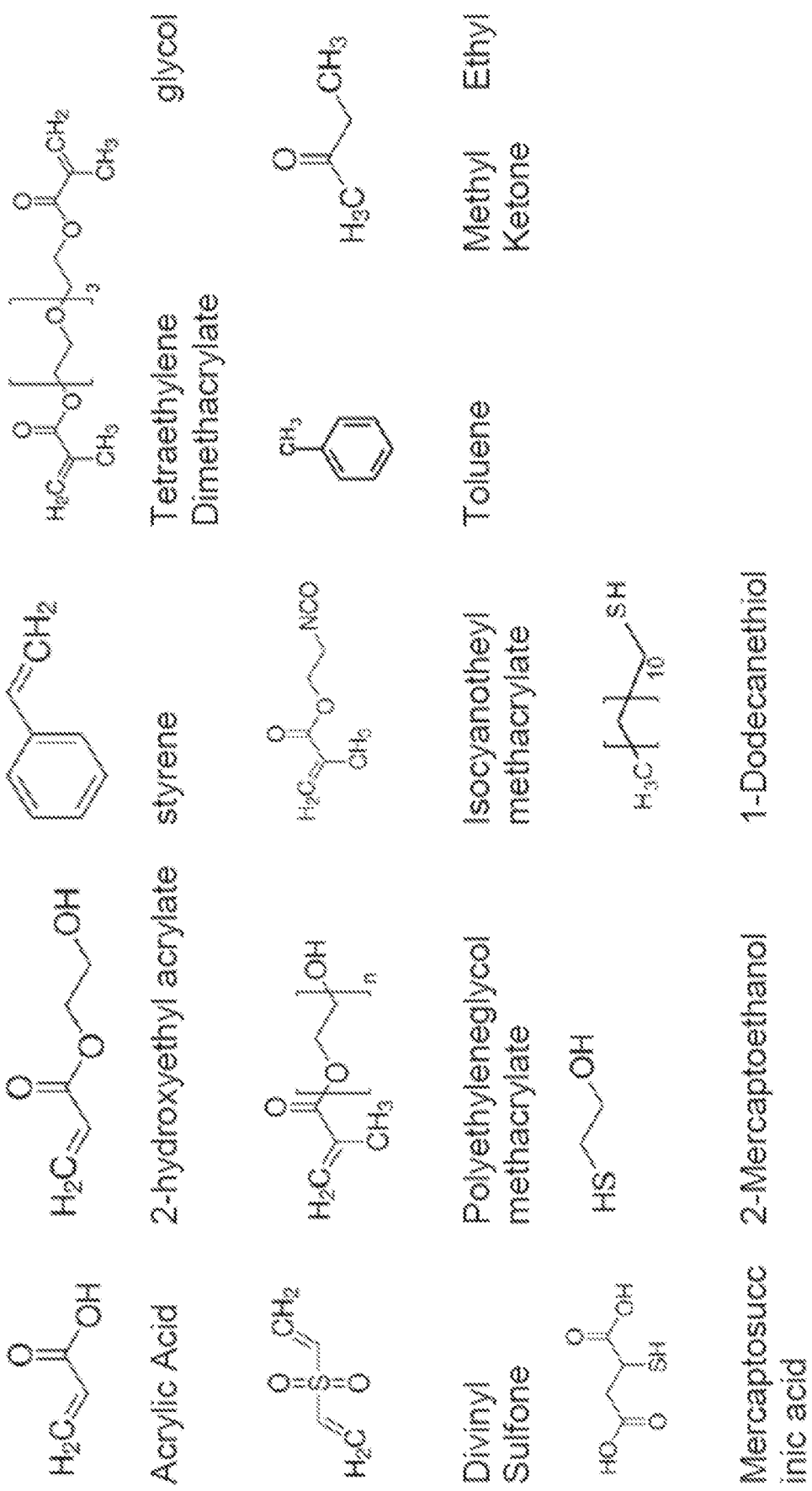
FIG. 10 depicts the mono and di-functional (meth)acrylates, CTAs, and solvents that can be utilized to synthesize hydrophilic, hydrophobic and amphiphilic nanogels of this disclosure.

The loading capacity (LC %) and encapsulation efficiency (EE %) of the NG depends on 1) the monomers that are chosen to form the bulk of the NG, 2) the type and concentration of CTA, 3) the solvent to monomer ratio within the solution polymerization protocol, and 4) the drug that is chosen for encapsulation. Although the optimal antibiotic LC and EE of the NGs will be ascertained based on the dose requirements of the infection, we will formulate CGKRK (SEQ ID NO:1)-NGs with LC≥15% and EE≥25% in order to enable efficient delivery of the antibiotic. The NG synthetic protocol can be tailored to maximize the LC % and EE % of two chosen antibiotics for this study, namely the water-soluble gentamicin and the water insoluble ciprofloxacin by choosing a combination of hydrophilic and hydrophobic monomers to encapsulate the drug. FIG. 10 depicts the chemical structures of the monomers, CTAs and solvents that can be utilized to achieve tailored NGs. A primary advantage of the NG approach for polymeric biomaterials development is that it allows combinations of comonomers that would otherwise be incompatible with the conditions encountered. Additionally, the mono to divinyl ratios of the monomers can also be varied to achieve tailored properties within the same combinations of monomers and solvents. To achieve the desired functional group conversion and the reaction kinetics and conversion measurements, FTIR will be used to monitor the methacrylic and acrylic conversion during polymerization reactions. High conversions and repeated precipitation will ensure that the amount of extractables will be minimal in these systems, and the extractables from the resin will also be quantified. Once the NGs have been isolated, triple detector GPC (for molecular weight, polydispersity, hydrodynamic radius, branching density), Dynamic Light Scattering and NMR (composition and residual polymerizable methacrylate concentration) will characterize the resulting nanogels. Post-conjugation with CGKRK peptide (SEQ ID NO:1) via the thiol methacrylate Michael addition reaction, the cytocompatibility of the NGs will be evaluated. To encapsulate the antibiotics, the NG compositions and the antibiotic will determine whether it will be freely water dispersible or will require a different carrier solvent (i.e. ethanol). Briefly, known concentrations of antibiotics gentamicin and ciprofloxacin will be dispersed in an appropriate solvent along with the NGs and stirred under ambient conditions to enable encapsulation via simple diffusion. After 24 hours, the mixture will be dialyzed (dialysis membrane-MWCO; 3.5 KDa) against deionized water for 48 h and then freeze-dried to obtain the gentamicin-loaded NGs (CGKRK (SEQ ID NO:1)-NG-Gent) and/or the ciprofloxacin-loaded NGs (CGKRK (SEQ ID NO:1)-NG-Cipro). The release of gentamicin and ciprofloxacin will be measured by incubating 1 mL of CGKRK (SEQ ID NO:1)-NGs at 10 mg/mL in phosphate buffered saline (PBS) (pH 7.4) at 37° C. using a dialysis cell with a 10,000 Da cutoff membrane. At each time point, the receiver compartment will be collected and replaced with fresh PBS. For gentamicin, the sampled receiver will be diluted 1:2 with 0.4 M boric acid pH 9.7 before derivatization with ortho-ophthaldehyde and the fluorescence measured at an excitation/emission wavelength ($\lambda ex/\lambda em$) of 360/460 nm will be compared to a calibration curve of gentamicin in 0.4 M boric acid pH 9.7. For ciprofloxacin, fluorescence $\lambda ex/\lambda em$ will be measured at a 278/440 nm and the average cumulative release will be plotted for each formulation and measured against a calibration curve.

Example 6

Optimizing the In-Vitro Release Kinetics NGs With Antibiotics

As a drug delivery mechanism that relies on simple diffusion to load and release the antibiotics, the NGs will need to be optimized to perform as successful sustained drug delivery vehicles. Therefore, the ability of the NGs to curb the burst release kinetics and enable the sustained release of the antibiotics from the NGs will be tailored to deliver therapeutic quantities of the antibiotics. The gentamicin and ciprofloxacin loaded NGs with functional methacrylic groups on the surface of the NG will be synthesized and their release rate as a function of UV exposure will be quantified using a microplate reader. Gentamicin fluorescence will be quantified at $\lambda ex/\lambda em$ of 360/460 nm while ciprofloxacin will be studied at $\lambda ex/\lambda em$ of 278/440 nm. The different NGs will then be evaluated for their ability to modulate drug release based on UV exposure. The drug release kinetics over a period of 1 week will be evaluated to quantify 1) if the drug released from the CGKRK (SEQ ID NO:1)-NG-Gent and CGKRK (SEQ ID NO:1)-NG-Cipro are of safe and therapeutically efficient doses and 2) if a combination of CGKRK (SEQ ID NO:1)-NG-Gent and CGKRK (SEQ ID NO:1)-NG-Cipro can be utilized to release the antibiotics in tandem to enable multi-drug delivery via this approach. At least 5 cytocompatible CGKRK (SEQ ID NO:1)-NGs are generated with enhanced drug loading capacities≥10% along with ability to vary the release kinetics of the antibiotic based on pre-exposure to UV (therapeutically relevant doses).

Example 7

Evaluation of the Binding and Penetration of Two Photoreactive NGs in an In-Vitro Cell Culture and Infection Model A transurethral catheterization procedure must deliver a therapeutic dose of antibiotics required to treat recurrent urinary tract infection (rUTI) via the NGs. We will implement an in-vitro infection model to test the ability of the CGKRK (SEQ ID NO:1)-NGs to treat biofilms and infected urothelial cells to establish the stability, binding efficiency and drug-delivery kinetics of the NGs within the challenging hydrodynamic environment of the bladder. The ability of the NG to effectively photo-crosslink and bind with the bladder urothelium will be established. Additionally, the ability of the NGs to 1) treat infected bladder epithelial cells and 2) treat infected, explanted murine bladders to deliver the antibiotics within a flow chamber (FC)-infection model for both UPEC and PA01 will be established. Unlike the infection model for UPEC, it was proposed that the biofilms on the catheters acted as a PA01 reservoirs, constantly releasing cells into the bladder. However, recent studies have shown that while the catheter can be replaced and/or coated with antibacterial agents to minimize biofilm formation, it is the ability of the PA01 bacteria to invade the bladder epithelium and subsequently grow to form a mature biofilm that is responsible for recurring infections. Therefore, it is the ability of the PA01 bacterial colonies to form biofilms within the urothelium that is critical step in propagating rUTI.

Figure 11:
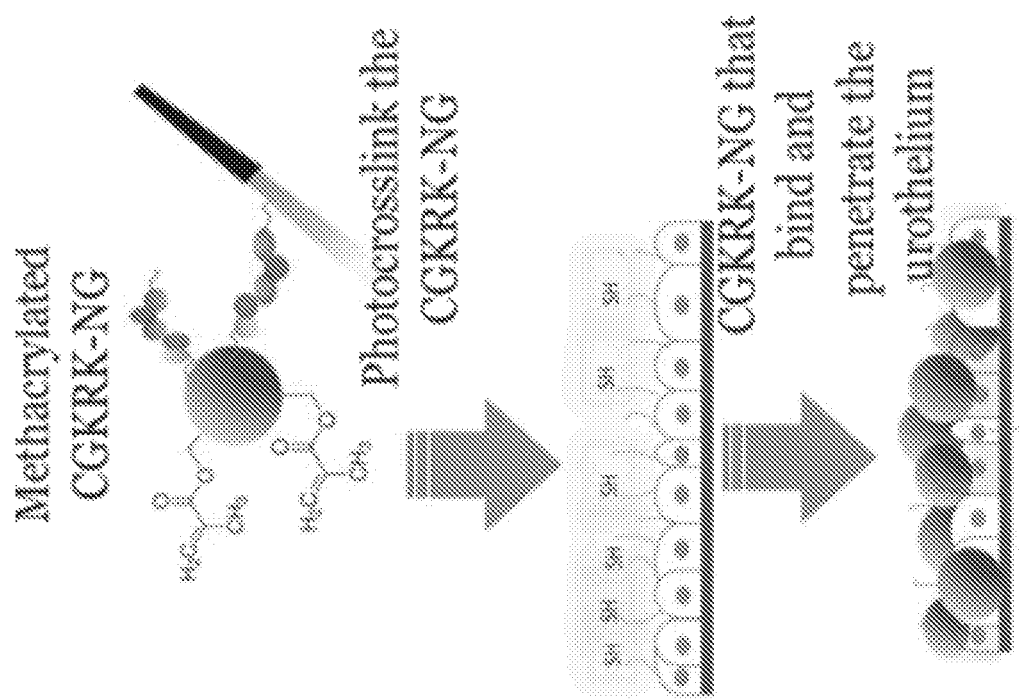
FIG. 11 depicts how the methacrylated CGKRK (SEQ ID NO:1)-NG can bind to the urothelium via photocrosslinking of the NG that may be initiated via a source of 380 nm light with fiber optic designed for bladder intravesical insertion.

In-vivo photocrosslinking studies: The ability of the CGKRK (SEQ ID NO:1)-NGs to bind and penetrate the urothelium for 24 h was studied by instilling the bladder with the FITC-tagged CGKRK (SEQ ID NO:1)-NG with 1 wt. % of the photoinitiator I2959 as depicted in FIG. 11. Photo-crosslinking was initiated via custom made fiber optic designed for murine bladder intravesical insertion at 380 nm UV exposure at 3 mW/cm-2. A protocol in which the photocrosslinking step was omitted was implemented as a control. LiCOR images of the FITC-tagged NGs showed significant accumulation in the urothelium after 24 hours while the control NG in the absence of UV exposure showed little accumulation. This in-vivo data indicates that: 1) photo-crosslinking the NGs to the urothelium serves as a source of local injury by disrupting the urothelial layer while tethering the NG to the bladder mucosal layers, and thereby enhancing the NG uptake within the bladder, and 2) the photo-crosslinking step prolonged the ability of the NG to remain within the bladder mucosal layers. This suggests that photo-crosslinking the CGKRK (SEQ ID NO:1)-linked NGs will enable the sustained delivery of the antibiotic within murine bladder and can be tailored to deliver the antibiotic over a period of time.

In-vitro static infection model studies: The ability of the CGKRK (SEQ ID NO:1)-NG2-Gent to affect a uropathogenic strain of E. coli UTI89 (ATCC 25922) and PA01 (ATCC 19660) grown in a static biofilm was evaluated. The bacterial inoculum (20 uL) was added to a flat bottom, clear 96-well sterile plate containing 180 uL of LB in wells for each and incubated at 37° C. without shaking for about 16 hrs to allow for the biofilm to form. To generate the UPEC biofilms, UTI89 with green fluorescence was produced by transformation with pEGFP (Clontech). When appropriate, gfp expression was induced from the pEGFP plasmid by addition of kanamycin (50 µg) to the growth medium. Both UTI89 and gfp-labeled PAO1 were grown separately overnight in LB at 37° C., diluted down to a starting inoculum of 2×105 CFU/ml (colony forming units per milliliter) and used directly as a seeding suspension. In order to determine the gentamicin minimal inhibitory concentration (MIC) and the gentamicin minimal bactericidal concentrations (MBC) for this study, the UTI89 and PAO1 biofilms were challenged with a range of gentamicin concentrations and subsequently challenged with the CGKRK (SEQ ID NO:1)-NG2-Gent systems of different LCs at 37° C. The treatments were compared to an untreated biofilm control and all samples for each condition were done in triplicate. The ability of the CGKRK (SEQ ID NO:1)-NG2-Gent to disrupt the biofilm over a 24 h period was quantified using a crystal violet assay and by quantifying the CFU after treatment. The CGKRK (SEQ ID NO:1)-NG2-Gent was able to successfully treat the biofilm in a dose-dependent manner, thereby indicating that CGKRK (SEQ ID NO:1)-NGs can treat biofilms once accessible.

Because a static biofilm in plastic is not equivalent to a biofilm inside a eukaryotic cell or a biofilm formed on a biotic surface, a static bacterial invasion survival assay utilizing the murine carcinoma bladder epithelium cell line MB49 was tested with the CGKRK (SEQ ID NO:1)-NG2-Gent. The cell line was maintained in DMEM medium with antibiotics and L-glutamine and seeded on 24-well plates for at least 24 hours to let the cells grow to confluence. Concurrently, biofilms of E. coli UTI89 was grown in 5 mL of LB at 37° C. in a static set-up. Triplicate sets of confluent MB49 bladder cell line was infected with UTI89-gfp using a multiplicity of infection of 15:1, as previously described bacteria per host cell. Infection was confirmed using fluorescence microscopy. Afterward, the plate was centrifuged at 600×g for 5 minutes and then incubated at 37° C. for 2 hours. Samples were subsequently washed with PBS2+ containing 0.9 mM Ca2+ and 0.9 mM of Mg2+ three times and cells were then incubated with DMEM with fetal bovine serum plus 100 µg/mL gentamicin to kill extracellular bacteria. This step was followed by three washes of PBS2+ and then adding a concentration of 10 µg/mL gentamicin to the culture media for 12 hours of gentamicin to kill extracellular bacteria. Samples were washed again three times with PBS2+ before adding fresh media along with the CGKRK (SEQ ID NO:1)-NG2-Gent and incubated for 12 hours. Subsequently, after lysing host cells with 0.4% Triton X-100 and serial dilutions onto LB agar plates, CFUs were counted. The results indicate that the CGKRK (SEQ ID NO:1)-NG2-Gent can penetrate the MB49 cells and to reach the biofilm to kill the intracellular-UTI89 in a dose-dependent manner.

Example 8

Establishing Photocrosslinking Conditions by Which Two NGs Can Stably Bind and Penetrate the Infected Bladder Epithelial Cells (BEC) to Deliver Antibiotics in Therapeutic Doses Optimizing the binding and penetrating efficiency of the NGs in a dynamic flow infection model will enable the delivery of therapeutic doses of antibiotics in a sustained manner and will be established over a test-period of 9 days. The model will be tested with CGKRK (SEQ ID NO:1)-NG-Gent and CGKRK (SEQ ID NO:1)-NG-Cipro and a combination of the two NGs. Experimental Design. To mimic the hydrodynamic challenges that the NGs will be exposed to, in-vivo, a custom flow chamber-infection model (FC) will be constructed within which human bladder epithelial cells (BEC) are placed to allow cultivation and imaging for extended periods of time. To-date, the FC model is the only in-vitro model in which the morphological alteration within the biofilms within the bladder in both early and later stages of colonization can be replicated for rUTI. The FC chamber allows for the continuous flow of medium, which enables the progression to secondary surface colonization events with biofilms.

Once the ability of the CGKRK (SEQ ID NO:1)-NG photo-crosslink within the FC cell model has been optimized and the dose requirements for the CGKRK (SEQ ID NO:1)-NG-Gent and CGKRK (SEQ ID NO:1)-NG-Cipro to treat the BEC-infection model has been established, the ability of NGs to work on ex vivo surgical explanted murine bladder infection model within the FC will be studied. Explants allow the ability to mimic many in-vivo conditions and is a necessary step to optimize our delivery system before moving to an in-vivo infection model. Murine bladders will be surgically explanted and placed within the FC chamber to allow cultivation and imaging for extended periods of time. Briefly, 3-7, 8-12-week-old C57BL/6 mice will be sacrificed via inhalation of CO2 and placed on a mouse-operating stage. The mice will be disinfected by spraying with isopropanol. To facilitate the removal of the urinary bladder, the ureters and urethra will be ligated with microsurgical clips and removed from the mouse. The organ will then be placed within the FC. A similar protocol as the static-FC BEC infection model will be followed for the remaining tests. Expected Outcomes. The conditions to optimize the photo-crosslinking of the NGs onto the bladder wall along with concentration and dose requirements of CGKRK (SEQ ID NO:1)-NG-Gent, CGKRK (SEQ ID NO:1)-NG-Cipro and a combination of the two NG to successfully treat the UPEC and PA01 infections within the FC cell model and the FC murine bladder model will be quantified and the data will be used to ascertain the doses for the in-vivo infection model.

Example 9

Evaluation and Optimization of the Ability of a One-Time Delivery of NG to Treat rUTI in a Mouse rUTI Model Once the in-vitro efficacy of the CGKRK (SEQ ID NO:1)-NGs is established, the efficacy of this approach to treat rUTI in a murine UTI model will be studied using a murine model in which the UPEC and PA01 strains will be utilized to colonize the urothelium in vivo and treated with CGKRK (SEQ ID NO:1)-NG-Gent and CGKRK (SEQ ID NO:1)-NG-Cipro and a combination of the two. To quantify the ability of two CGKRK (SEQ ID NO:1)-NGs to treat rUTI in-vivo and test therapeutic efficacy compared to the current standard of care treatments for rUTI (oral and IV antibiotics). Briefly, 7 to 8-week-old female mice (C57BL/6) will be infected with $1-2 \times 10^7$ CFU or $2 \times 10^6$ CFU per mouse of either UPEC or PAO1, respectively. Negative controls will include 1) mock-infection controls in which mice inoculated with 50 µl sterile phosphate buffered saline (PBS); 2) mice infected with each organism but not treated and; 3) mice infected with each organism and treated with CGKRK (SEQ ID NO:1)-NG alone. Although within an hour after infection, up to 1000-fold reduction in bacterial load is lost via micturition, it is assumed that 50% of the bacteria will be still be present within intracellular niches as observed by time-lapse fluorescence video microscopy of infected bladders. Additionally, enumeration assays of viable bacteria within the mouse bladder and the kidney tissues reveals high levels of bacteria at 6 hours post inoculation. The antibiotic treatments will be initiated 3 days later, allowing time for biofilm colonies to first establish mature reservoir populations within the bladder. The antibiotic treatment groups will consist of: 1) animals infected with each organism and given IV gentamicin; 2) animals infected with each organism and given oral gentamicin; 3) animals infected with each organism with CGKRK (SEQ ID NO:1)-NG-Gent introduced into the bladder; 4) animals infected with each organism with CGKRK (SEQ ID NO:1)-NG-Cipro introduced into the bladder, and 5) animals infected with each organism with CGKRK (SEQ ID NO:1)-NG-Gent/Cipro introduced into the bladder. The NGs antibiotic treatment will be administered to infected mice via transurethral catheterization procedure in which a lubricated 24 G Angiocath catheter without the needle will be inserted via the urethra into the bladder cavity to wash the bladder once with 50 µL PBS. As a focal injury on the urothelium is a necessary condition for the CGKRK peptide (SEQ ID NO:1) to bind to the urothelium, three circular motions will be made on the cell layer via the catheter tip at the time of delivery. Subsequently, a 1 mL syringe filled with 100 µL of the CGKRK (SEQ ID NO:1)-NG-Gent or CGKRK (SEQ ID NO:1)-NG-Cipro solution (0.3 mg/ml in PBS/20% DMSO) CGKRK (SEQ ID NO:1)-NG-Gent/CGKRK (SEQ ID NO:1)-NG-Cipro combination will be attached to the catheter and approximately 50 µL of the solution was injected into the bladder until complete distension (determined by abdominal palpation). The catheter with an attached syringe will be left in the bladder for 15 min. After an additional 3 days without antibiotic treatments (9 days total post inoculation), mice will be sacrificed and bacterial titers present within the bladders enumerated. The antibiotic concentrations employed in the in-vivo assays were will be based on the doses established from the in-vitro tests on infected murine bladders while the oral and IV antibiotics will be administered as per antibiotic concentrations based on standard doses given to human patients scaled down for use in mice. Additionally, disc diffusion assays with urine specimens collected from treated mice will be used to confirm that the antibiotic reached concentrations in the urine that were sufficient to kill free-living UTI89 and PA01. Specifically, within 2 h post administration, effective antibiotic concentrations in the urine will be quantified by collecting urine specimens from mice by gently pressing their bladders over clean plastic wrap. The 10 mL aliquots of urine collected will be spotted onto 7-mm-diameter circular pieces of sterile filter paper and placed on freshly plated UPEC and PA01 colonies spread on LB agar plates. Using filter discs of known antibiotic concentrations to generate standard curves, the diameter of clearance around each disc was measured after a 24-h incubation at 37° C. are calculated quantify the antibiotic levels in the urine specimens. Dino-Lite camera AM4113T-GRFBY model equipped with 480 nm (GFP) and 570 nm (Texas Red) excitation filters and 510 nm long-pass and 610 nm long pass emission filters will be utilized to provide visualization of the bacteria in the infected bladders. The abdominal cavity will be opened by incision, and that bladder will be imaged at 20-40× magnification. The bladders will be subsequently harvested aseptically, weighed, and homogenized in 1 ml PBS containing 0.025% Triton X-100. Bacterial titers within the homogenates will be determined by plating serial dilutions on LB agar plates. To study the histology of the bladder, freshly removed bladders will be washed in PBS and snap-frozen in liquid nitrogen. The tissue will be embedded in OCT media (manufacturer) and cryosectioned in 7-µm consecutive steps so that one section is placed on a slide for fluorescence imaging and the next section will be placed on another slide for hematoxylin-eosin staining. The tissue will be mounted with appropriate medium (VECTASHIELD™ antifade mounting medium with DAPI for fluorescence imaging, or Permount™ medium (Thermo-Fisher) for H&E staining and covered with coverslip. The bladders will be imaged with a Nikon E600 upright fluorescence microscope with SPOT RT color camera. The images in each fluorescence channel will be acquired under saturation as 12-bit gray TIFF, and H&E images were acquired as RGB images. Each low magnification image covering the entire bladder area will be analyzed with ImageJ software. The background will be subtracted with ProcessMath Subtract tool, and the integrated gray density per image will be calculated using Measure tool. The intensities will be plotted as individual values using Prism software. The results show antibiotic loaded CGKRK (SEQ ID NO:1)-NGs are more effective for treating rUTI infections.

The foregoing discussion of the disclosure has been presented for purposes of illustration and description. The foregoing is not intended to limit the disclosure to the form or forms, or embodiment or embodiments, disclosed herein. In the foregoing Detailed Description, various features of the disclosure are grouped together in one or more embodiments for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment. Thus, the following claims are incorporated into this disclosure, with each claim standing on its own as a separate preferred embodiment of the disclosure.

Moreover, though the present disclosure has included description of one or more embodiments and certain variations and modifications, other variations and modifications are within the scope of the disclosure, as may be within the skill and knowledge of those skilled in the art after understanding the present disclosure. It is intended to obtain rights which include alternative embodiments to the extent permitted, including alternate, interchangeable, or equivalent structures, functions, ranges, or steps to those claimed, whether or not such alternate, interchangeable, or equivalent structures, functions, ranges, or steps are disclosed herein, and without intending to dedicate to the public any patentable subject matter.

The invention claimed is:
1. A method for synthesizing nanogels, the method comprising:
   conducting a polymerization reaction in polymerization solution to form nanogels, wherein the polymerization solution comprises
      a monomer mixture that comprises one or more monovinyl monomers and one or more divinyl monomers; and
   a polymerization solvent;
   wherein the monovinyl monomer comprises 2-hydroxyethyl acrylate (HEA) and acrylic acid (AA);
   wherein the divinyl monomer comprises tetraethylene glycol dimethacrylate (TTEGDMA); wherein the polymerization solution further comprises an initiator that is azobisisobutyronitrile (AIBN) and a chain transfer agent that is 2-mercaptoethanol (ME); and
   wherein the polymerization solution has a solvent:monomer mixture mass ratio in a range of about 2:1 to about 8:1;
   conducting a photoactive functionalization reaction to bind photoactive functional groups to the nanogels, wherein the photoactive functional groups bound to the nanogels are suitable for photo-induced internal cross-linking within individual nanogels and external cross-linking between nanogels, thereby synthesizing the nanogels that are photoactive;
   conducting a surface conjugation of ligands reaction to bind one or more cell-penetrating peptides to the surfaces of the nanogels wherein the surface conjugation of ligands reaction is conducted by methacrylate functionalization, which comprises binding methacrylate functional groups to residual hydroxyl groups on the nanogels and binding the cell penetrating peptides via a thio-methacrylate Michael addition reaction, and wherein the cell-penetrating peptide(s) are CGKRK (SEQ ID NO: 1);
   loading the nanogels with a therapeutic/diagnostic agent, wherein the loading is accomplished by dispersing the nanogels in the loading solution thereby swelling the nanogels and increasing the sizes of pores of the nanogels such that the therapeutic/diagnostic agent diffuses through the pores into interior volumes of the swollen nanogels, and wherein the therapeutic/diagnostic agent is one or more antibiotics; and
   conducting a photo-induced aggregation reaction of the nanogels loaded with the therapeutic/diagnostic agent by exposing the nanogels to light that activates the photoactive functional groups bound to the nanogels thereby causing the internal crosslinking within individual nanogels and the external crosslinking between nanogels.

2. A method for synthesizing nanogels, the method comprising:
conducting a polymerization reaction in polymerization solution to form nanogels, wherein the polymerization solution comprises
a monomer mixture that comprises one or more monovinyl monomers and one or more divinyl monomers; and
a polymerization solvent
wherein the monovinyl monomer(s) are 2-hydroxyethyl acrylate (HEA) and acrylic acid (AA), and the divinyl monomer(s) are tetraethylene glycol dimethacrylate (TTEGDMA); and
wherein the polymerization solution has a solvent:monomer mixture mass ratio of at least about 2:1;
conducting a photoactive functionalization reaction to bind photoactive functional groups to the nanogels, wherein the photoactive functional groups bound to the nanogels are suitable for photo-induced internal crosslinking within individual nanogels and external crosslinking between nanogels, thereby synthesizing the nanogels that are photoactive; and
conducting a surface conjugation of ligands reaction to bind one or more cell-penetrating peptides to the surfaces of the nanogels;
wherein the cell-penetrating peptide comprises CGKRK (SEQ ID NO: 1); and
loading the nanogels with a therapeutic/diagnostic agent, wherein the loading is accomplished by dispersing the nanogels in a loading solution thereby swelling the nanogels and increasing the sizes of the pores of the nanogels such that the therapeutic/diagnostic agent diffuses through the pores into the interior volumes of the swollen nanogels; wherein the therapeutic/diagnostic agent comprises gentamicin.

* * * * *